(12) United States Patent
Nakahara et al.

(10) Patent No.: US 10,071,175 B2
(45) Date of Patent: Sep. 11, 2018

(54) FILTER AND CONTAINER HAVING MICROBICIDAL ACTIVITY

(71) Applicant: Sharp Kabushiki Kaisha, Osaka-shi, Osaka (JP)

(72) Inventors: Takahiro Nakahara, Osaka (JP); Miho Yamada, Osaka (JP); Kiyoshi Minoura, Osaka (JP); Seiji Takami, Osaka (JP)

(73) Assignee: SHARP KABUSHIKI KAISHA, Osaka-Shi, Osaka (JP)

( * ) Notice: Subject to any disclaimer, the term of this patent is extended or adjusted under 35 U.S.C. 154(b) by 165 days.

(21) Appl. No.: 14/897,252

(22) PCT Filed: Mar. 12, 2015

(86) PCT No.: PCT/JP2015/057327
§ 371 (c)(1),
(2) Date: Dec. 10, 2015

(87) PCT Pub. No.: WO2015/166725
PCT Pub. Date: Nov. 5, 2015

(65) Prior Publication Data
US 2016/0121005 A1    May 5, 2016

(30) Foreign Application Priority Data

Apr. 28, 2014 (JP) .................................. 2014-093185
Aug. 25, 2014 (JP) .................................. 2014-170692

(51) Int. Cl.
*A61L 2/02* (2006.01)
*A61L 9/16* (2006.01)
(Continued)

(52) U.S. Cl.
CPC ................. *A61L 2/02* (2013.01); *A61L 2/022* (2013.01); *A61L 9/16* (2013.01); *B01D 29/31* (2013.01);
(Continued)

(58) Field of Classification Search
None
See application file for complete search history.

(56) References Cited

U.S. PATENT DOCUMENTS

2003/0164326 A1*  9/2003  Eberl ..................... B01D 39/00
                                                    210/263
2003/0205475 A1   11/2003  Sawitowski
(Continued)

FOREIGN PATENT DOCUMENTS

AU       2013903399        9/2013
CN        201329050 Y     10/2009
(Continued)

OTHER PUBLICATIONS

E. P. Ivanova, "Bactericidal activity of black silicon", Nature Communications, Published Nov. 26, 2013, 19 pgs, Macmillan Publishers Limited.
(Continued)

*Primary Examiner* — Benjamin M Kurtz
(74) *Attorney, Agent, or Firm* — Harness, Dickey and Pierce, P.L.C.

(57) ABSTRACT

A sterilization filter includes a synthetic polymer film, the synthetic polymer film having a surface which has a plurality of first raised portions, a two-dimensional size of the plurality of first raised portions being more than 20 nm and less than 500 μm when viewed in a normal direction. The synthetic polymer film is arranged in a predetermined shape. In the arrangement of the predetermined shape, an inclination of a normal to the surface varies depending on a position
(Continued)

over the surface, and an inclination of a normal to a surface opposite to the surface varies depending on a position over the opposite surface. At least part of the surface is capable of coming into contact with a gas or liquid.

22 Claims, 18 Drawing Sheets

(51) Int. Cl.
    *A61L 2/232*     (2006.01)
    *B01D 63/14*     (2006.01)
    *B01D 69/02*     (2006.01)
    *B01D 69/04*     (2006.01)
    *B01D 71/06*     (2006.01)
    *B01D 57/02*     (2006.01)
    *B01D 29/31*     (2006.01)
    *B01D 39/16*     (2006.01)
    *B01D 46/00*     (2006.01)
    *B29C 35/08*     (2006.01)
    *B29C 59/04*     (2006.01)
    *B01D 69/06*     (2006.01)

(52) U.S. Cl.
    CPC ......... *B01D 39/1692* (2013.01); *B01D 57/02* (2013.01); *B01D 63/14* (2013.01); *B01D 69/02* (2013.01); *B01D 69/04* (2013.01); *B01D 69/06* (2013.01); *B01D 71/06* (2013.01); *A61L 2/232* (2013.01); *A61L 2209/14* (2013.01); *B01D 46/0028* (2013.01); *B01D 2279/65* (2013.01); *B01D 2323/08* (2013.01); *B01D 2323/42* (2013.01); *B01D 2323/48* (2013.01); *B29C 59/046* (2013.01); *B29C 2035/0827* (2013.01)

(56) References Cited

U.S. PATENT DOCUMENTS

| | | | |
|---|---|---|---|
| 2007/0159698 | A1 | 7/2007 | Taguchi et al. |
| 2009/0252825 | A1 | 10/2009 | Taguchi et al. |
| 2010/0009137 | A1 | 1/2010 | Kodama |
| 2010/0203161 | A1 | 8/2010 | Gehri et al. |
| 2010/0234323 | A1 | 9/2010 | Holzl et al. |
| 2011/0235181 | A1 | 9/2011 | Hayashibe et al. |
| 2011/0281068 | A1 | 11/2011 | David et al. |
| 2012/0318772 | A1 | 12/2012 | Minoura et al. |
| 2013/0057958 | A1 | 3/2013 | Minoura et al. |
| 2013/0344290 | A1 | 12/2013 | Yu et al. |
| 2014/0004304 | A1 | 1/2014 | Yu et al. |
| 2014/0077418 | A1 | 3/2014 | Otani et al. |
| 2015/0140154 | A1 | 5/2015 | Isurugi et al. |
| 2015/0168610 | A1 | 6/2015 | Fukui et al. |
| 2015/0273755 | A1 | 10/2015 | Yee et al. |
| 2016/0212989 | A1* | 7/2016 | Juodkazis ............ A01N 25/34 |

FOREIGN PATENT DOCUMENTS

| | | | |
|---|---|---|---|
| EP | 2979844 | A1 | 2/2016 |
| JP | 08-024843 | A | 1/1996 |
| JP | 2005-055114 | A | 3/2005 |
| JP | 2008-024843 | | 2/2008 |
| JP | 2008-197217 | A | 8/2008 |
| JP | 4265729 | B2 | 5/2009 |
| JP | 2009-166502 | A | 7/2009 |
| JP | 2010-000719 | A | 1/2010 |
| JP | 2010079200 | A | 4/2010 |
| JP | 2012078438 | A | 4/2012 |
| JP | 2012/514239 | A | 6/2012 |
| JP | 2012-208169 | A | 10/2012 |
| JP | 2013033287 | A | 2/2013 |
| JP | 2013-078573 | A | 5/2013 |
| JP | 2014-029391 | A | 2/2014 |
| JP | 2014/029391 | A | 2/2014 |
| JP | 2014-066975 | A | 4/2014 |
| JP | 2014-509967 | A | 4/2014 |
| JP | 2014-511779 | A | 5/2014 |
| JP | 2014-202955 | A | 10/2014 |
| JP | 2015-024549 | A | 2/2015 |
| WO | WO-2007/097454 | A1 | 8/2007 |
| WO | WO-2011/125486 | A1 | 10/2011 |
| WO | WO-2011/148721 | A1 | 12/2011 |
| WO | WO-2012/161315 | A1 | 11/2012 |
| WO | WO-2013/183576 | A1 | 12/2013 |
| WO | WO-2013/191092 | A1 | 12/2013 |
| WO | WO-2014/021376 | A1 | 2/2014 |
| WO | WO-2014/171365 | A1 | 10/2014 |
| WO | WO-2015/163018 | A1 | 10/2015 |

OTHER PUBLICATIONS

International Search Report PCT/ISA/210 for International Application No. PCT/JP2015/057327 dated Jun. 3, 2015.
Trafton, A., (2006) "MIT's Anti-Microbial 'Paint' Kills Flu, Bacteria" http://chemistry.mit.edu/mits-anti-microbial-paint-kills-flu-bacteria, p. 2-4.
Good Housekeeping (2011) "Do-It-All Cleaning Guide" http://www.goodhousekeeping.com/home/cleaning/tips/a18875/how-to-clean/, p. 1-12.
Office Action dated Mar. 9, 2017 issued in U.S. Appl No. 15/386,131.
Yao, C. et al., "Decreased bacteria density on nanostructured polyurethane," Society for Biomaterials, pp. 1823-1828, Jun. 29, 2013.
Ivanova, E. et al., "Natural Bactericidal Surfaces: Mechanical Rupture of Pseudomonas aeruginosa Cells by Cicada Wings," Small Journal, pp. 1-6, 2012.
Office Action dated Dec. 29, 2016 issued in U.S. Appl. No. 14/771,833.
E. P. Ivanova, "Bactericidal activity of black silicon", Nature Communications, Published Nov. 26, 2013, 19pgs, Macmillan Publishers Limited.
Epstein, A.K. et al., "Liquid-infused structured surfaces with exceptional anti-biofouling performance," PNAS, Aug. 14, 2012, vol. 109, No. 33.
Restriction Requirement dated Oct. 27, 2016 for corresponding U.S. Appl. No. 14/771,833.
Compound Summary for CID 3086063, Tecoflex from PubChem, accessed Jan. 17, 2018.
Espeel, P. et al., (2013) "One-pot, additive-free preparation of functionalized polyurethanes via amine-thiol-ene conjugation" Polymer Chemistry 4:2449.
Office Action dated Jan. 24, 2018 issued in U.S. Appl. No. 15/126,078.
Pogodin, S. et al. (2013) "Biophysical Model of Bacterial Cell Interactions with Nanopatterned Cicada Wing Surfaces" Biophysical Journal 104: 835-840.
Office Action dated Dec. 11, 2017 issued in U.S. Appl. No. 15/592,922.
International Search Report PCT/ISA/210 for International Application No. PCT/JP2015/081608 dated Feb. 3, 2016.
Office Action dated Jun. 14, 2018 issued in U.S. Appl. No. 15/592,922.
Office Action dated Jul. 13, 2018 issued in U.S. Appl. No. 15/784,771.

* cited by examiner

FIG.2B
(a)
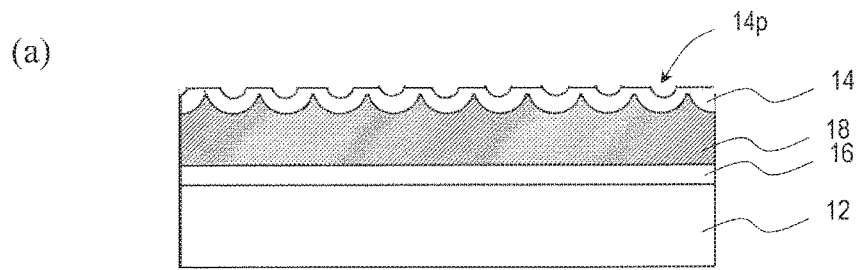
(b)
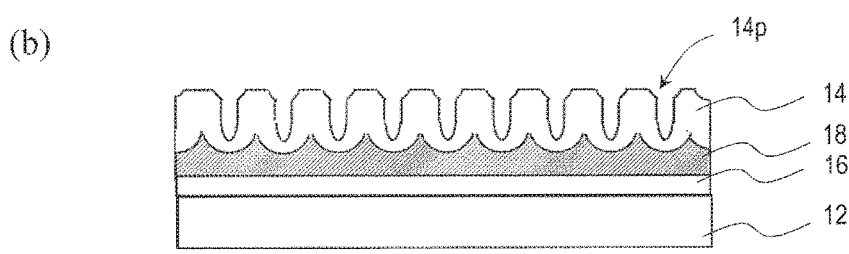
(c)
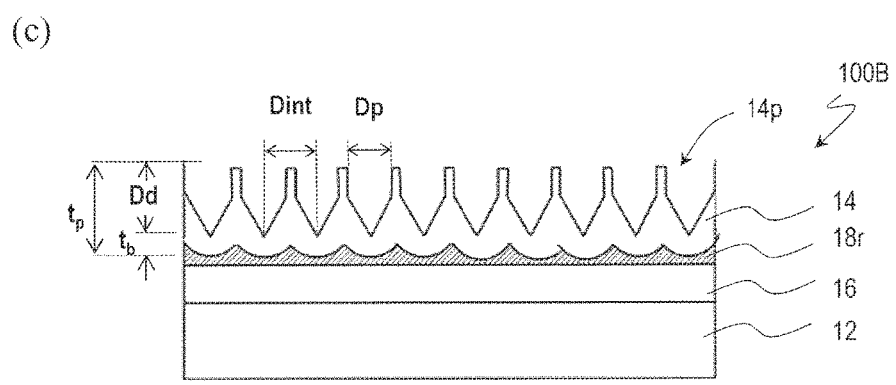

FIG.4
(a)
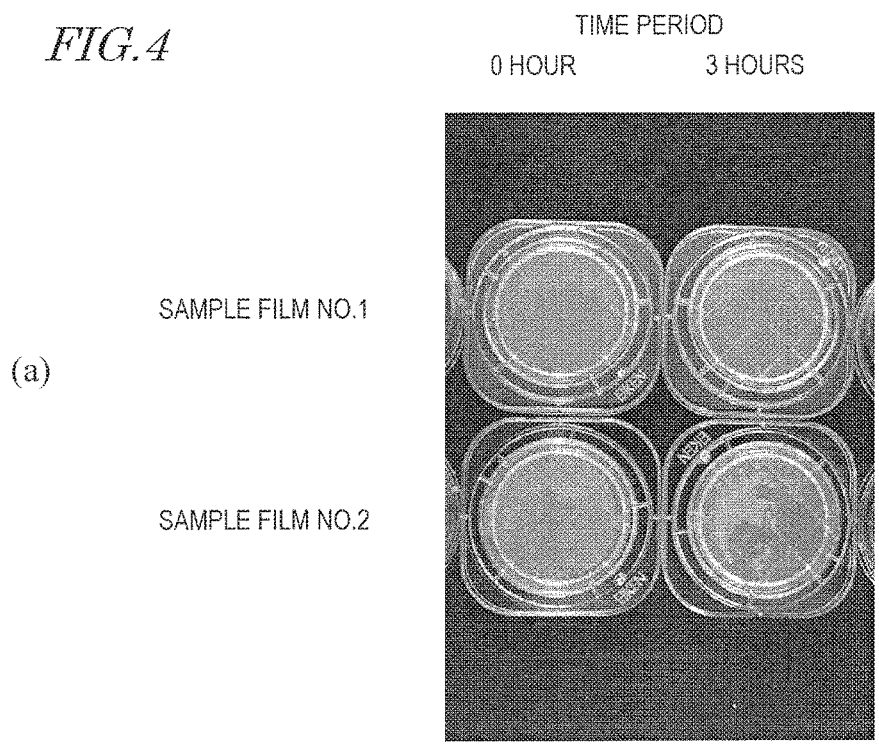
(b)
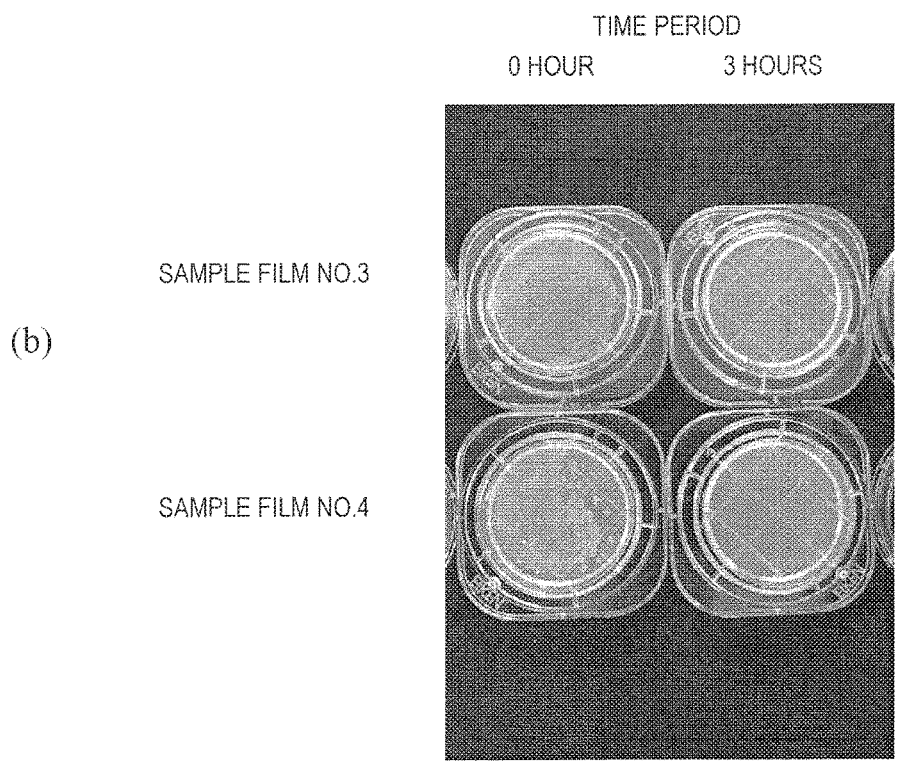

FIG.5
(a)
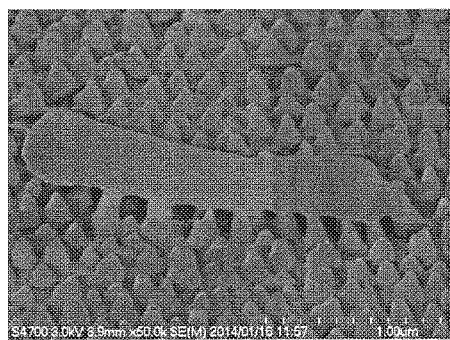
(c)
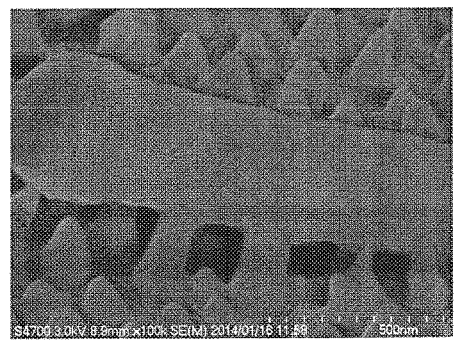
(b)
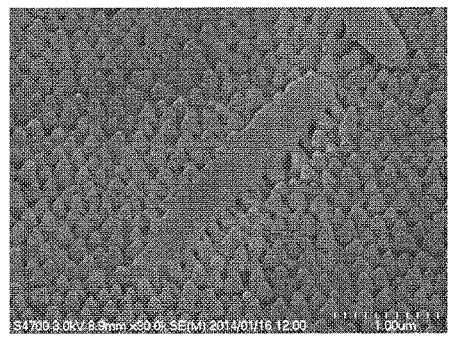
(d)
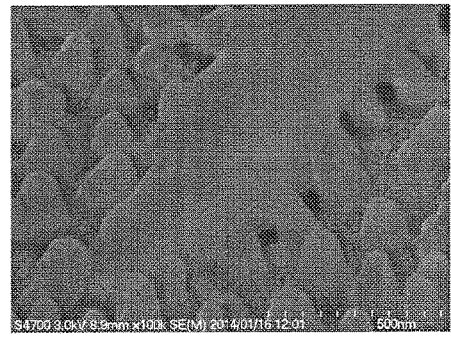

FIG.6
(a)
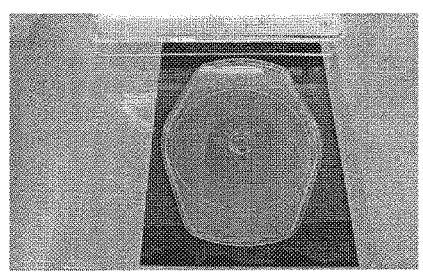
(b)
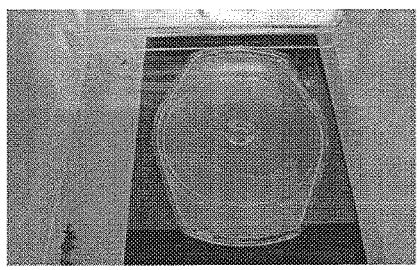
(c)
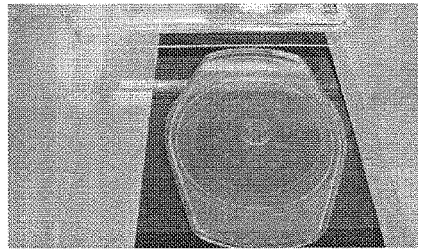
(d)
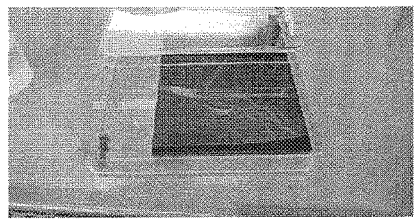
(e)
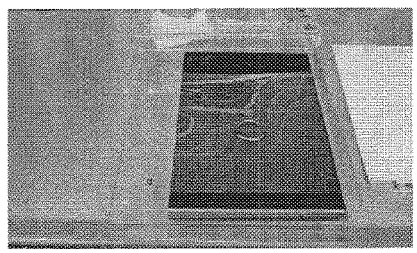
(f)
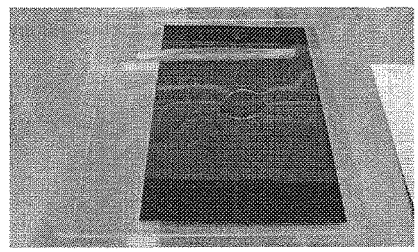

FIG. 7
(a) 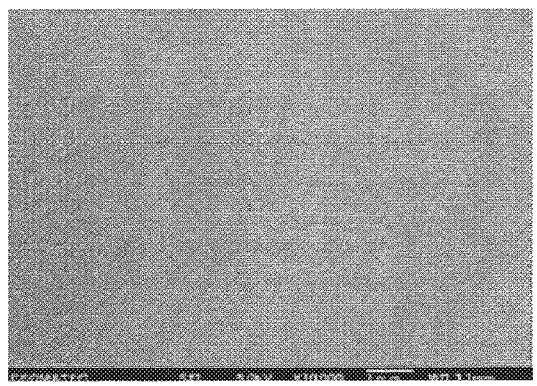
(b) 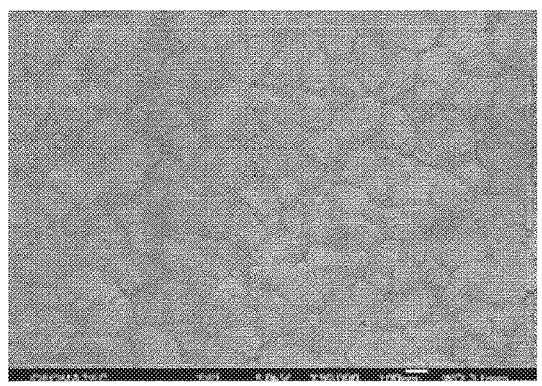
(c) 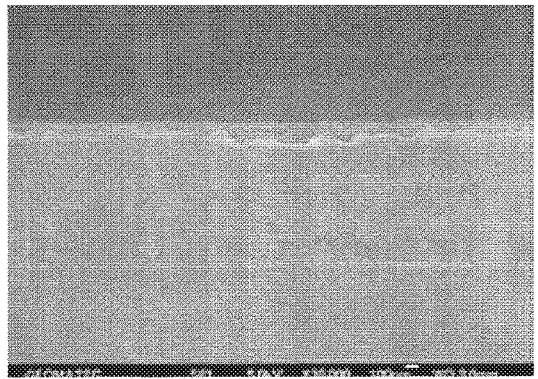

FIG.12
(a)
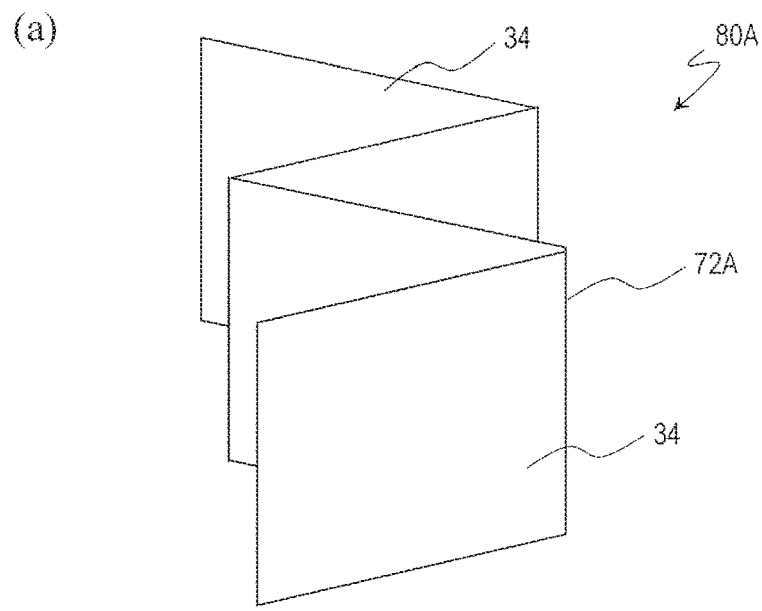
(b)
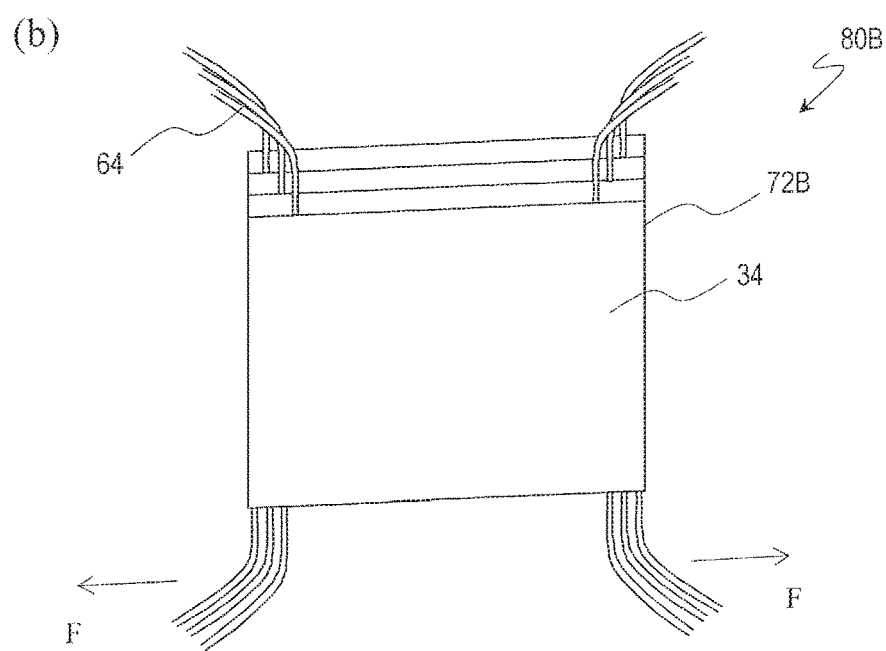

FIG.14
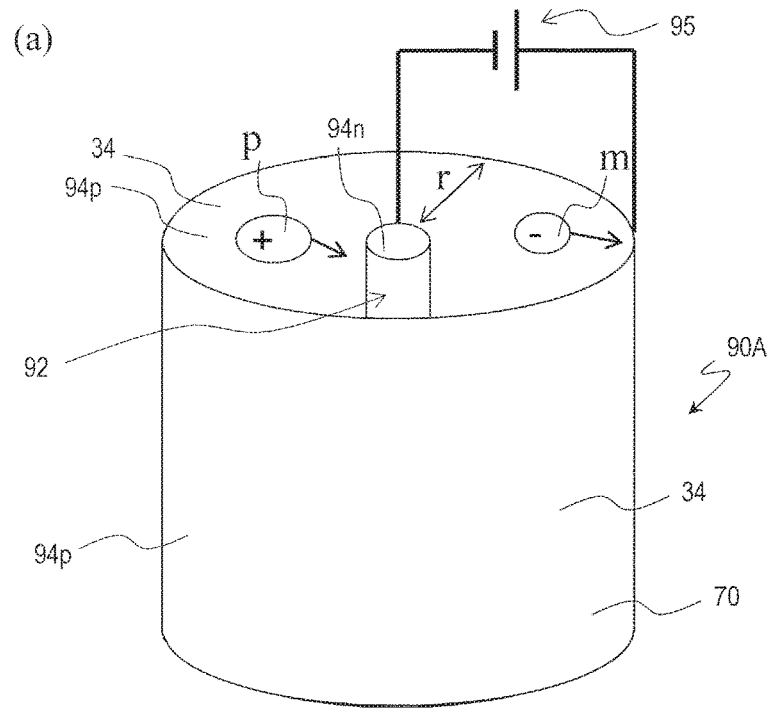
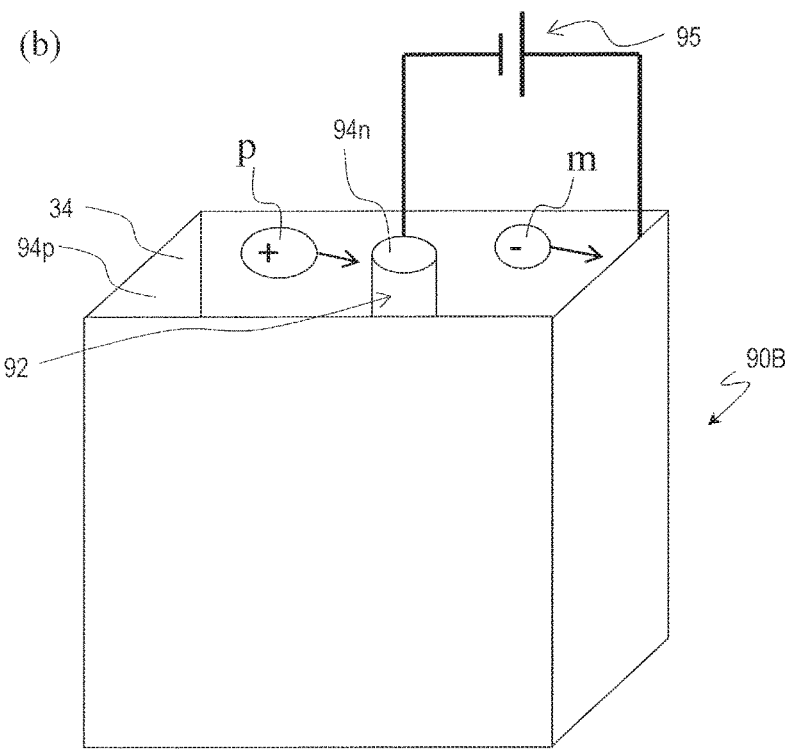

FIG.15
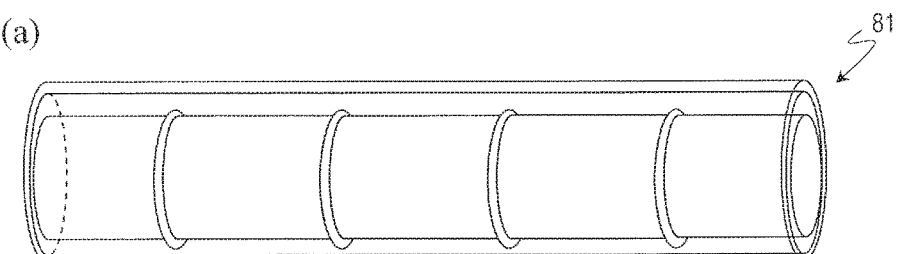
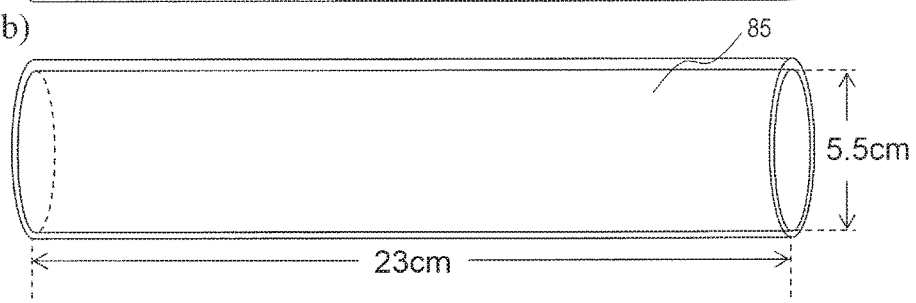
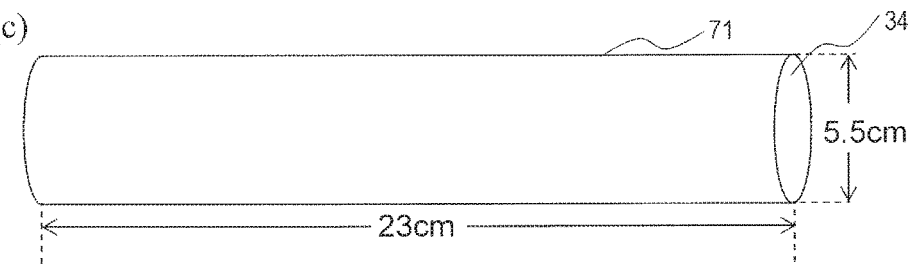
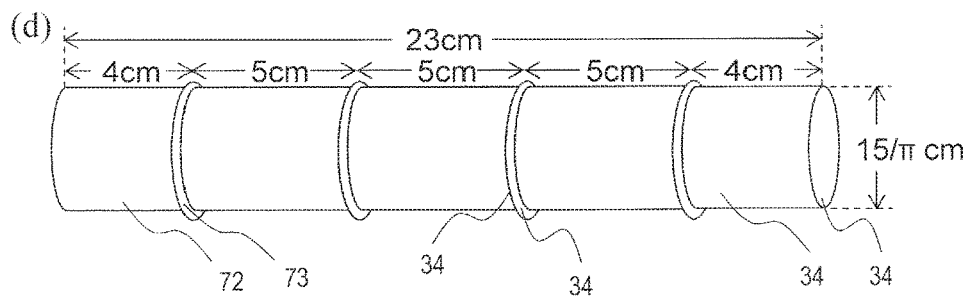
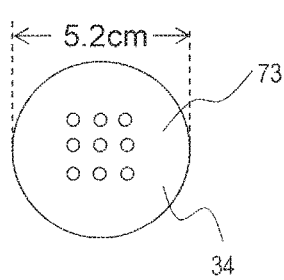

FIG.16

FIG.17
(a)
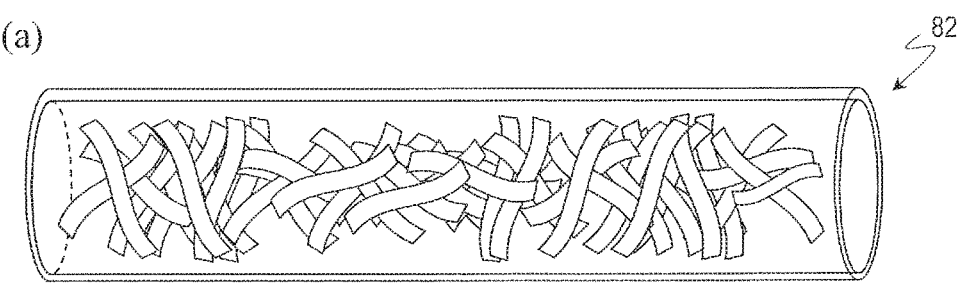
(b)
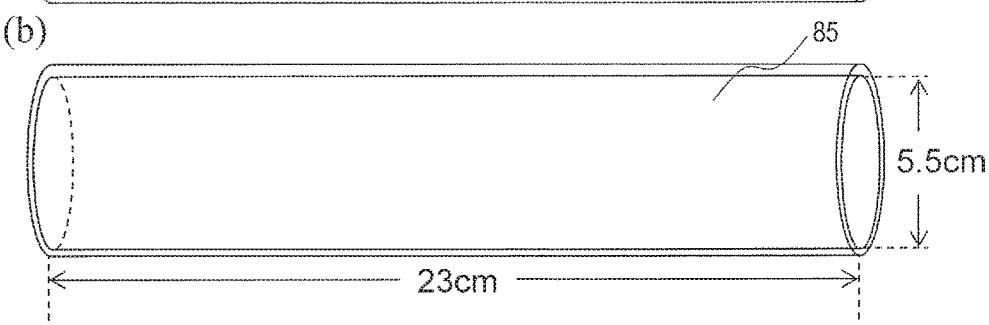
(c)
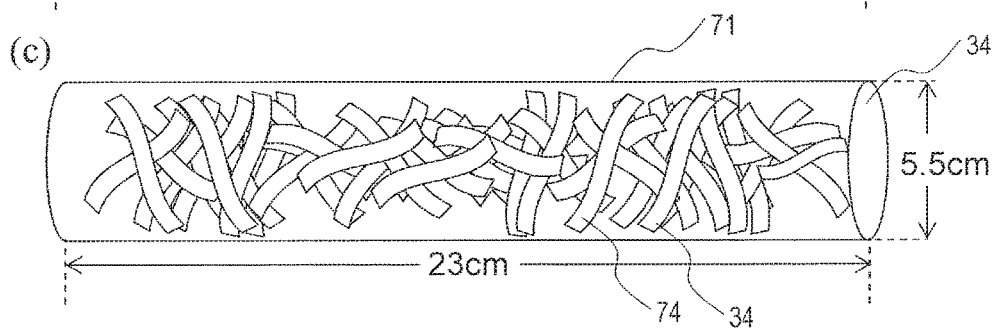

FILTER AND CONTAINER HAVING MICROBICIDAL ACTIVITY

TECHNICAL FIELD

The present invention relates to a filter and container which have a microbicidal activity. The present invention also relates to a synthetic polymer film whose surface has a microbicidal activity, a sterilization method with the use of the surface of the synthetic polymer film, a mold for production of the synthetic polymer film, and a mold manufacturing method. In this specification, the "mold" includes molds that are for use in various processing methods (stamping and casting), and is sometimes referred to as a stamper. The "mold" can also be used for printing (including nanoimprinting).

BACKGROUND ART

Recently, it was reported that surficial nanostructures of black silicon, wings of cicadas and dragonflies have a bactericidal activity (Non-patent Document 1). For example, reportedly, black silicon has 500 nm high nanopillars, and the physical structure of the nanopillars produces a bactericidal activity. Wings of cicadas and dragonflies have 240 nm high nanopillars.

According to Non-patent Document 1, black silicon has the strongest bactericidal activity on Gram-negative bacteria, while wings of dragonflies have a weaker bactericidal activity, and wings of cicadas have a still weaker bactericidal activity. The static contact angle (hereinafter, simply referred to as "contact angle") of the black silicon surface with respect to water is 80°, while the contact angles of the surface of wings of dragonflies and cicadas with respect to water are 153° and 159°, respectively.

CITATION LIST

Patent Literature

Patent Document 1: Japanese Patent No. 4265729
Patent Document 2: Japanese Laid-Open Patent Publication No. 2009-166502
Patent Document 3: WO 2011/125486
Patent Document 4: WO 2013/183576

Non-Patent Literature

Non-patent Document 1: Ivanova, E. P. et al., "Bactericidal activity of black silicon", Nat. Commun. 4:2838 doi: 10.1038/ncomms3838 (2013).

SUMMARY OF INVENTION

Technical Problem

The mechanism of killing bacteria by nanopillars is not clear from the results described in Non-patent Document 1. It is also not clear whether the reason why black silicon has a stronger bactericidal activity than wings of dragonflies and cicadas resides in the difference in height or shape of nanopillars or the difference in surface free energy (which can be evaluated by the contact angle).

The bactericidal activity of black silicon is difficult to utilize because black silicon is poor in mass productivity, and is hard but brittle so that the shapability is poor.

The present invention was conceived for the purpose of solving the above problems. The major objects of the present invention include providing a synthetic polymer film whose surface has a microbicidal activity, a sterilization method with the use of the surface of the synthetic polymer film, a mold for production of the synthetic polymer film, and a mold manufacturing method and providing a filter or container in which the synthetic polymer film whose surface has a microbicidal activity is used.

Solution to Problem

A synthetic polymer film according to an embodiment of the present invention is a synthetic polymer film including a surface which has a plurality of first raised portions, wherein a two-dimensional size of the plurality of first raised portions is in a range of more than 20 nm and less than 500 nm when viewed in a normal direction of the synthetic polymer film; and the surface has a microbicidal effect.

In one embodiment, a static contact angle of the surface with respect to hexadecane is not more than 51°.

In one embodiment, an adjoining distance of the plurality of first raised portions is more than 20 nm and not more than 1000 nm.

In one embodiment, a height of the plurality of first raised portions is not less than 50 nm and less than 500 nm. The height of the plurality of first raised portions may be not more than 150 nm.

In one embodiment, the synthetic polymer film further includes a plurality of second raised portions superimposedly formed over the plurality of first raised portions, wherein a two-dimensional size of the plurality of second raised portions is smaller than the two-dimensional size of the plurality of first raised portions and does not exceed 100 nm.

In one embodiment, the plurality of second raised portions include a generally conical portion.

In one embodiment, a height of the plurality of second raised portions is more than 20 nm and not more than 100 nm.

A method for sterilizing a gas or liquid according to an embodiment of the present invention includes bringing the gas or liquid into contact with the surface of any of the above-described synthetic polymer films.

A mold according to an embodiment of the present invention includes a surface, the surface having a plurality of first recessed portions and a plurality of second recessed portions formed in the plurality of first recessed portions, wherein a two-dimensional size of the plurality of first recessed portions is in a range of more than 20 nm and less than 500 nm when viewed in a normal direction of the surface of the mold, and a two-dimensional size of the plurality of second recessed portions is smaller than the two-dimensional size of the plurality of first recessed portions and does not exceed 100 nm.

A mold manufacturing method according to an embodiment of the present invention is a method for manufacturing the above-described mold, including: (a) a step of providing an aluminum base or an aluminum film deposited on a support; (b) an anodization step of applying a voltage at a first level while a surface of the aluminum base or the aluminum film is kept in contact with an electrolytic solution, thereby forming a porous alumina layer which has first recessed portions; (c) after step (b), an etching step of bringing the porous alumina layer into contact with an etching solution, thereby enlarging the first recessed portions; and (d) after step (c), applying a voltage at a second level which is lower than the first level while the porous alumina layer is kept in contact with an electrolytic solution, thereby forming second recessed portions in the first recessed portions.

In one embodiment, the first level is higher than 40 V, and the second level is equal to or lower than 20 V.

In one embodiment, the electrolytic solution is an oxalic acid aqueous solution.

A sterilization filter and a container according to an embodiment of the present invention include any of the above-described synthetic polymer films.

A sterilization filter according to an embodiment of the present invention includes a synthetic polymer film, the synthetic polymer film having a surface which has a plurality of first raised portions, a two-dimensional size of the plurality of first raised portions being more than 20 nm and less than 500 μm when viewed in a normal direction, wherein the synthetic polymer film is arranged in a predetermined shape, in the arrangement of the predetermined shape, an inclination of a normal to the surface varies depending on a position over the surface, and an inclination of a normal to a surface opposite to the surface varies depending on a position over the opposite surface, and at least part of the surface is capable of coming into contact with a gas or liquid.

In one embodiment, in the arrangement of the predetermined shape, a cross section of the synthetic polymer film forms at least one ring.

In one embodiment, in the arrangement of the predetermined shape, a cross section of the synthetic polymer film forms a spiral.

In one embodiment, the predetermined shape is a bellows-like shape.

In one embodiment, the surface further has a plurality of spacer portions.

In one embodiment, a height of the plurality of spacer portions is not less than 1 μm.

In one embodiment, the plurality of spacer portions have a pillar-like shape.

In one embodiment, the sterilization filter further includes a spacer, wherein the spacer is arranged so as to form a space above the surface of the synthetic polymer film.

In one embodiment, the spacer is in the form of a thread.

In one embodiment, the sterilization filter further includes at least one electrode which is in contact with the synthetic polymer film.

In one embodiment, at least part of the surface of the synthetic polymer film is positively charged.

In one embodiment, at least part of a surface opposite to the surface of the synthetic polymer film is negatively charged.

In one embodiment, the predetermined shape is a cylindrical shape, the synthetic polymer film demarcates a cylinder, and a plurality of synthetic polymer film pieces are provided in the cylinder, each of the plurality of synthetic polymer film pieces having a surface which has the plurality of first raised portions.

In one embodiment, a sum of an area per 1 cm$^3$ of an inner volume of the cylinder of the surface of the synthetic polymer film and an area per 1 cm$^3$ of an inner volume of the cylinder of the surfaces of the plurality of synthetic polymer film pieces is not less than 4.4 cm$^2$.

In one embodiment, the synthetic polymer film further has a plurality of second raised portions superimposedly formed over the plurality of first raised portions, and a two-dimensional size of the plurality of second raised portions is smaller than the two-dimensional size of the plurality of first raised portions and does not exceed 100 nm.

A container according to an embodiment of the present invention includes a synthetic polymer film on at least part of an inner wall, the synthetic polymer film having a plurality of first raised portions over its surface, a two-dimensional size of the plurality of first raised portions being more than 20 nm and less than 500 nm when viewed in a normal direction. The container may include the synthetic polymer film on a bottom surface.

Advantageous Effects of Invention

According to an embodiment of the present invention, a synthetic polymer film whose surface has a microbicidal activity, a sterilization method with the use of the surface of the synthetic polymer film, a mold for production of the synthetic polymer film, and a mold manufacturing method are provided. According to another embodiment of the present invention, a filter or container in which the synthetic polymer film whose surface has a microbicidal activity is used is provided.

BRIEF DESCRIPTION OF DRAWINGS

FIG. 2B (*a*) to (*c*) are diagrams for illustrating a method for manufacturing a moth-eye mold 100B and a configuration of the moth-eye mold 100B.

FIGS. 4 (*a*) and (*b*) are pictures for illustrating the evaluation results of the microbicidal ability of sample films No. 1 to No. 4 and are, specifically, optical images of the surfaces of agar media on which *Pseudomonas aeruginosa* (or "*P. aeruginosa*") bacteria were cultured. The upper part of (a) shows the evaluation results of sample film No. 1 (the time period that the sample film was left: 0 hour (5 minutes), 3 hours). The lower part of (a) shows the evaluation results of sample film No. 2 (the time period: 0 hour (5 minutes), 3 hours). The upper part of (b) shows the evaluation results of sample film No. 3 (the time period: 0 hour (5 minutes), 3 hours). The lower part of (b) shows the evaluation results of sample film No. 4 (the time period: 0 hour (5 minutes), 3 hours).

FIG. 5 (*a*) to (*d*) show SEM images obtained by SEM (Scanning Electron Microscope) observation of a *P. aeruginosa* bacterium which died at a surface which had a moth-eye structure.

FIG. 6 Pictures for illustrating the results of examinations as to the microbicidal activity achieved by the moth-eye structure. (a) shows the state of sample film No. 1 with a cover. (b) shows the state of comparative example 1 with a cover. (c) shows the state of comparative example 2 with a cover. (d) shows the state of sample film No. 1 without a cover. (e) shows the state of comparative example without a cover. (f) shows the state of comparative example 2 without a cover.

FIG. 7 (*a*) shows a SEM image of a surface of an aluminum base. (b) shows a SEM image of a surface of an aluminum film. (c) shows a SEM image of a cross section of the aluminum film.

FIGS. 12 (a) and (b) are schematic diagrams showing other sterilization filters according to an embodiment of the present invention.

FIG. 14 (a) is a schematic diagram showing a sterilization filter which utilizes electrophoresis according to an embodiment of the present invention. (b) is a schematic diagram showing a microbicidal container which utilizes electrophoresis according to an embodiment of the present invention.

FIG. 15 (a) to (e) are schematic diagrams for illustrating the configuration of a sterilization filter 81 of example 1.

FIG. 16 A schematic diagram for illustrating an experimental system.

FIG. 17 (a) to (c) are schematic diagrams for illustrating the configuration of a sterilization filter 82 of Example 2.

DESCRIPTION OF EMBODIMENTS

Figure 1:
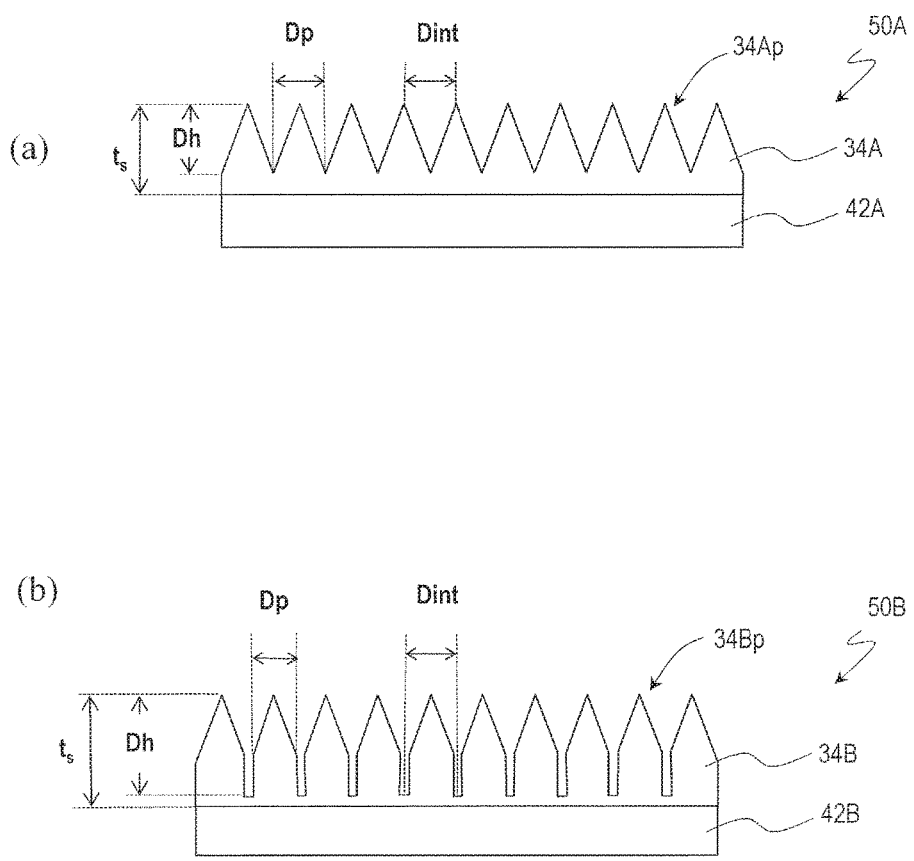
FIGS. 1 (*a*) and (*b*) are schematic cross-sectional views of synthetic polymer films 34A and 34B, respectively, according to embodiments of the present invention.

Hereinafter, a synthetic polymer film whose surface has a microbicidal effect, a sterilization method with the use of the surface of the synthetic polymer film, a mold for production of the synthetic polymer film, and a mold manufacturing method according to embodiments of the present invention are described with reference to the drawings.

In this specification, the following terms are used.

"Sterilization" (or "microbicidal") means reducing the number of proliferative microorganisms contained in an object, such as solid or liquid, or a limited space, by an effective number.

"Microorganism" includes viruses, bacteria, and fungi.

"Antimicrobial" generally includes suppressing and preventing multiplication of microorganisms and includes suppressing dinginess and slime which are attributed to microorganisms.

The present applicant conceived a method for producing an antireflection film which has a moth-eye structure (antireflection surface) with the use of an anodized porous alumina layer. Using the anodized porous alumina layer enables manufacture of a mold which has an inverted moth-eye structure with high mass-productivity (e.g., Patent Documents 1 to 4). The entire disclosures of Patent Documents 1 to 4 are incorporated by reference in this specification. Note that antireflection films which are placed over the surface of liquid crystal television displays manufactured and sold until now by the present applicant are hydrophilic. This is for the purpose of facilitating wiping away of grease, such as fingerprint, adhered to the moth-eye structure. If the moth-eye structure is not hydrophilic, an aqueous washing solution cannot effectively enter the gap between raised portions of the moth-eye structure so that the grease cannot be wiped away.

The present inventors developed the above-described technology and arrived at the concept of a synthetic polymer film whose surface has a microbicidal effect.

The configuration of a synthetic polymer film according to an embodiment of the present invention is described with reference to FIGS. 1(a) and 1(b).

FIGS. 1(a) and 1(b) respectively show schematic cross-sectional views of synthetic polymer films 34A and 34B according to embodiments of the present invention. The synthetic polymer films 34A and 34B described herein as examples are formed on base films 42A and 42B, respectively, although the present invention is not limited to these examples. The synthetic polymer films 34A and 34B can be directly formed on a surface of an arbitrary object.

A film 50A shown in FIG. 1(a) includes a base film 42A and a synthetic polymer film 34A provided on the base film 42A. The synthetic polymer film 34A has a plurality of raised portions 34Ap over its surface. The plurality of raised portions 34Ap constitute a moth-eye structure. When viewed in a normal direction of the synthetic polymer film 34A, the two-dimensional size of the raised portions 34Ap, Dp, is in the range of more than 20 nm and less than 500 nm. Here, the "two-dimensional size" of the raised portions 34Ap refers to the diameter of a circle equivalent to the area of the raised portions 34Ap when viewed in a normal direction of the surface. When the raised portions 34Ap have a conical shape, for example, the two-dimensional size of the raised portions 34Ap is equivalent to the diameter of the base of the cone. The typical adjoining distance of the raised portions 34Ap, Dint, is more than 20 nm and not more than 1000 nm. When the raised portions 34Ap are densely arranged so that there is no gap between adjoining raised portions 34Ap (e.g., the bases of the cones partially overlap each other) as shown in FIG. 1(a), the two-dimensional size of the raised portions 34Ap, Dp, is equal to the adjoining distance Dint. The typical height of the raised portions 34Ap, Dh, is not less than 50 nm and less than 500 nm. As will be described later with experimental examples, a microbicidal activity is exhibited even when the height Dh of the raised portions 34Ap is not more than 150 nm. The thickness of the synthetic polymer film 34A, $t_s$, is not particularly limited but only needs to be greater than the height Dh of the raised portions 34Ap.

The surface of the synthetic polymer film 34A has a microbicidal ability. As will be described later with reference to FIGS. 5(a) to 5(d), the raised portions 34Ap break, for example, the cell walls of *P. aeruginosa* that is one of the Gram-negative bacteria, thereby killing *P. aeruginosa* bacteria.

The synthetic polymer film 34A shown in FIG. 1(a) has the same moth-eye structure as the antireflection films disclosed in Patent Documents 1 to 4. From the viewpoint of producing an antireflection function, it is preferred that the surface has no flat portion, and the raised portions 34Ap are densely arranged over the surface. Further, the raised portions 34Ap preferably has a such shape that the cross-sectional area (a cross section parallel to a plane which is orthogonal to an incoming light ray, e.g., a cross section parallel to the surface of the base film 42A) increases from the air side to the base film 42A side, e.g., a conical shape. From the viewpoint of suppressing interference of light, it is preferred that the raised portions 34Ap are arranged without regularity, preferably randomly. However, these features are unnecessary when only the microbicidal activity of the synthetic polymer film 34A is pursued. For example, the raised portions 34Ap do not need to be densely arranged. The raised portions 34Ap may be regularly arranged. Note that, however, the shape and arrangement of the raised portions 34Ap are preferably selected such that the raised portions 34Ap effectively act on microorganisms.

A film 50B shown in FIG. 1(b) includes a base film 42B and a synthetic polymer film 34B provided on the base film 42B. The synthetic polymer film 34B has a plurality of raised portions 34Bp over its surface. The plurality of raised portions 34Bp constitute a moth-eye structure. In the film 50B, the configuration of the raised portions 34Bp of the synthetic polymer film 34B is different from that of the raised portions 34Ap of the synthetic polymer film 34A of the film 50A. Descriptions of features which are common with those of the film 50A are sometimes omitted.

When viewed in a normal direction of the synthetic polymer film 34B, the two-dimensional size of the raised portions 34Bp, Dp, is in the range of more than 20 nm and less than 500 nm. The typical adjoining distance of the raised portions 34Bp, Dint, is more than 20 nm and not more than 1000 nm, and Dp<Dint holds. That is, in the synthetic polymer film 34B, there is a flat portion between adjoining raised portions 34Bp. The raised portions 34Bp have the shape of a cylinder with a conical portion on the air side. The typical height of the raised portions 34Bp, Dh, is not less than 50 nm and less than 500 nm. The raised portions 34Bp may be arranged regularly or may be arranged irregularly. When the raised portions 34Bp are arranged regularly, Dint also represents the period of the arrangement. This also applies to the synthetic polymer film 34A, as a matter of course.

In this specification, the "moth-eye structure" includes not only surficial nanostructures that have an excellent antireflection function and that are formed by raised portions which have such a shape that the cross-sectional area (a cross section parallel to the film surface) increases as do the raised portions 34Ap of the synthetic polymer film 34A shown in FIG. 1(a) but also surficial nanostructures that are formed by raised portions which have a part where the cross-sectional area (a cross section parallel to the film surface) is constant as do the raised portions 34Bp of the synthetic polymer film 34B shown in FIG. 1(b). Note that, from the viewpoint of breaking the cell walls and/or cell membranes of microorganisms, providing a conical portion is preferred. Note that, however, the tip end of the conical shape does not necessarily need to be a surficial nanostructure but may have a rounded portion (about 60 nm) which is generally equal to the nanopillars which form surficial nanostructures of the wings of cicadas.

The surfaces of the synthetic polymer films 34A and 34B may be treated when necessary. For example, a mold releasing agent or surface treatment agent may be applied to the surfaces in order to modify the surface tension (or surface free energy). Some types of the mold releasing agent or surface treatment agent lead to formation of a thin polymer film over the surfaces of the synthetic polymer films 34A and 34B. Alternatively, the surfaces of the synthetic polymer films 34A and 34B may be modified using plasma or the like. For example, by a plasma treatment using a gas which contains fluorine, lipophilicity can be given to the surfaces of the synthetic polymer films 34A and 34B. When the surfaces of the synthetic polymer films 34A and 34B have lipophilicity, the surfaces can have a relatively strong microbicidal activity.

A mold for forming the moth-eye structure such as illustrated in FIGS. 1(a) and 1(b) over the surface (hereinafter, referred to as "moth-eye mold") has an inverted moth-eye structure obtained by inverting the moth-eye structure. Using an anodized porous alumina layer which has the inverted moth-eye structure as a mold without any modification enables inexpensive production of the moth-eye structure. Particularly when a moth-eye mold in the shape of a hollow cylinder is used, the moth-eye structure can be efficiently manufactured according to a roll-to-roll method. Such a moth-eye mold can be manufactured according to methods disclosed in Patent Documents 2 to 4.

A manufacturing method of a moth-eye mold 100A that is for production of the synthetic polymer film 34A is described with reference to FIGS. 2A(a) to 2A(e).

Figure 2A:
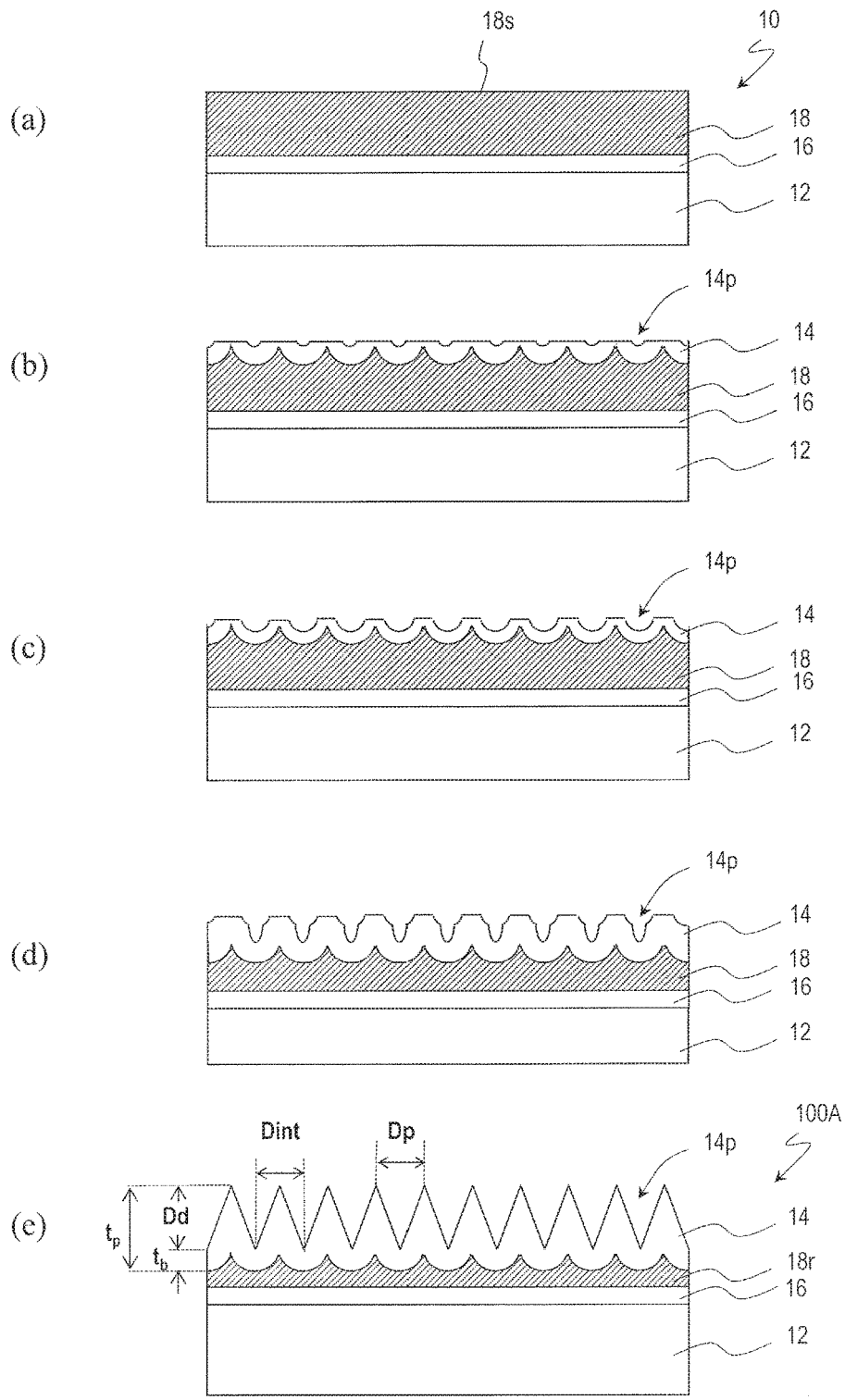
FIG. 2A (*a*) to (*e*) are diagrams for illustrating a method for manufacturing a moth-eye mold 100A and a configuration of the moth-eye mold 100A.

Firstly, a mold base 10 is provided which includes an aluminum base 12, an inorganic material layer 16 provided on a surface of the aluminum base 12, and an aluminum film 18 deposited on the inorganic material layer 16 as shown in FIG. 2A(a).

The aluminum base 12 used may be an aluminum base whose aluminum purity is not less than 99.50 mass % and less than 99.99 mass % and which has relatively high rigidity. The impurity contained in the aluminum base 12 may preferably include at least one element selected from the group consisting of iron (Fe), silicon (Si), copper (Cu), manganese (Mn), zinc (Zn), nickel (Ni), titanium (Ti), lead (Pb), tin (Sn) and magnesium (Mg). Particularly, Mg is preferred. Since the mechanism of formation of pits (hollows) in the etching step is a local cell reaction, the aluminum base 12 ideally does not contain any element which is nobler than aluminum. It is preferred that the aluminum base 12 used contains, as the impurity element, Mg (standard electrode potential: −2.36 V) which is a base metal. If the content of an element nobler than aluminum is 10 ppm or less, it can be said in terms of electrochemistry that the aluminum base 12 does not substantially contain the element. The Mg content is preferably 0.1 mass % or more of the whole. It is, more preferably, in the range of not more than about 3.0 mass %. If the Mg content is less than 0.1 mass %, sufficient rigidity cannot be obtained. On the other hand, as the Mg content increases, segregation of Mg is more likely to occur. Even if the segregation occurs near a surface over which a moth-eye mold is to be formed, it would not be detrimental in terms of electrochemistry but would be a cause of a defect because Mg forms an anodized film of a different form from that of aluminum. The content of the impurity element may be appropriately determined depending on the shape, thickness, and size of the aluminum base 12, in view of required rigidity. For example, when the aluminum base 12 in the form of a plate is prepared by rolling, the appropriate Mg content is about 3.0 mass %. When the aluminum base 12 having a three-dimensional structure of, for example, a hollow cylinder is prepared by extrusion, the Mg content is preferably 2.0 mass % or less. If the Mg content exceeds 2.0 mass %, the extrudability deteriorates in general.

The aluminum base 12 used may be an aluminum pipe in the shape of a hollow cylinder which is made of, for example, JIS A1050, an Al—Mg based alloy (e.g., JIS A5052), or an Al—Mg—Si based alloy (e.g., JIS A6063).

The surface of the aluminum base 12 is preferably a surface cut with a bit. If, for example, abrasive particles are remaining on the surface of the aluminum base 12, conduction will readily occur between the aluminum film 18 and the aluminum base 12 in a portion in which the abrasive particles are present. Not only in the portion in which the abrasive particles are remaining but also in a portion which has a roughened surface, conduction readily occurs between the aluminum film 18 and the aluminum base 12. When conduction occurs locally between the aluminum film 18 and the aluminum base 12, there is a probability that a local cell reaction will occur between an impurity in the aluminum base 12 and the aluminum film 18.

The material of the inorganic material layer 16 may be, for example, tantalum oxide ($Ta_2O_5$) or silicon dioxide ($SiO_2$). The inorganic material layer 16 can be formed by, for example, sputtering. When a tantalum oxide layer is used as the inorganic material layer 16, the thickness of the tantalum oxide layer is, for example, 200 nm.

The thickness of the inorganic material layer 16 is preferably not less than 100 nm and less than 500 nm. If the thickness of the inorganic material layer 16 is less than 100 nm, there is a probability that a defect (typically, a void; i.e., a gap between crystal grains) occurs in the aluminum film 18. If the thickness of the inorganic material layer 16 is not less than 500 nm, insulation is likely to occur between the aluminum base 12 and the aluminum film 18 due to the surface condition of the aluminum base 12. To realize anodization of the aluminum film 18 by supplying an electric current from the aluminum base 12 side to the aluminum film 18, the electric current needs to flow between the aluminum base 12 and the aluminum film 18. When employing a configuration where an electric current is supplied from the inside surface of the aluminum base 12 in the shape of a hollow cylinder, it is not necessary to provide an electrode to the aluminum film 18. Therefore, the aluminum film 18 can be anodized across the entire surface, while such a problem does not occur that supply of the electric current becomes more difficult as the anodization advances. Thus, the aluminum film 18 can be anodized uniformly across the entire surface.

To form a thick inorganic material layer 16, it is in general necessary to increase the film formation duration. When the film formation duration is increased, the surface temperature of the aluminum base 12 unnecessarily increases, and as a result, the film quality of the aluminum film 18 deteriorates, and a defect (typically, a void) occurs in some cases. When the thickness of the inorganic material layer 16 is less than 500 nm, occurrence of such a problem can be suppressed.

The aluminum film 18 is, for example, a film which is made of aluminum whose purity is not less than 99.99 mass % (hereinafter, sometimes referred to as "high-purity aluminum film") as disclosed in Patent Document 3. The aluminum film 18 is formed by, for example, vacuum evaporation or sputtering. The thickness of the aluminum film 18 is preferably in the range of not less than about 500 nm and not more than about 1500 nm. For example, the thickness of the aluminum film 18 is about 1 μm.

The aluminum film 18 may be an aluminum alloy film disclosed in Patent Document 4 in substitution for the high-purity aluminum film. The aluminum alloy film disclosed in Patent Document 4 contains aluminum, a metal element other than aluminum, and nitrogen. In this specification, the "aluminum film" includes not only the high-purity aluminum film but also the aluminum alloy film disclosed in Patent Document 4.

Using the above-described aluminum alloy film enables to obtain a specular surface whose reflectance is not less than 80%. The average grain diameter of crystal grains that form the aluminum alloy film when viewed in the normal direction of the aluminum alloy film is, for example, not more than 100 nm, and that the maximum surface roughness Rmax of the aluminum alloy film is not more than 60 nm. The content of nitrogen in the aluminum alloy film is, for example, not less than 0.5 mass % and not more than 5.7 mass %. It is preferred that the absolute value of the difference between the standard electrode potential of the metal element other than aluminum which is contained in the aluminum alloy film and the standard electrode potential of aluminum is not more than 0.64 V, and that the content of the metal element in the aluminum alloy film is not less than 1.0 mass % and not more than 1.9 mass %. The metal element is, for example, Ti or Nd. The metal element is not limited to these examples but may be such a different metal element that the absolute value of the difference between the standard electrode potential of the metal element and the standard electrode potential of aluminum is not more than 0.64 V (for example, Mn, Mg, Zr, V, and Pb). Further, the metal element may be Mo, Nb, or Hf. The aluminum alloy film may contain two or more of these metal elements. The aluminum alloy film is formed by, for example, a DC magnetron sputtering method. The thickness of the aluminum alloy film is also preferably in the range of not less than about 500 nm and not more than about 1500 nm. For example, the thickness of the aluminum alloy film is about 1 μm.

Then, a surface 18s of the aluminum film 18 is anodized to form a porous alumina layer 14 which has a plurality of recessed portions (micropores) 14p as shown in FIG. 2A(b). The porous alumina layer 14 includes a porous layer which has the recessed portions 14p and a barrier layer (the base of the recessed portions (micropores) 14p). As known in the art, the interval between adjacent recessed portions 14p (the distance between the centers) is approximately twice the thickness of the barrier layer and is approximately proportional to the voltage that is applied during the anodization. This relationship also applies to the final porous alumina layer 14 shown in FIG. 2A(e).

The porous alumina layer 14 is formed by, for example, anodizing the surface 18s in an acidic electrolytic solution. The electrolytic solution used in the step of forming the porous alumina layer 14 is, for example, an aqueous solution which contains an acid selected from the group consisting of oxalic acid, tartaric acid, phosphoric acid, sulfuric acid, chromic acid, citric acid, and malic acid. For example, the surface 18s of the aluminum film 18 is anodized with an applied voltage of 80 V for 55 seconds using an oxalic acid aqueous solution (concentration: 0.3 mass %, solution temperature: 10° C.), whereby the porous alumina layer 14 is formed.

Then, the porous alumina layer 14 is brought into contact with an alumina etchant such that a predetermined amount is etched away, whereby the opening of the recessed portions 14p is enlarged as shown in FIG. 2A(c). By modifying the type and concentration of the etching solution and the etching duration, the etching amount (i.e., the size and depth of the recessed portions 14p) can be controlled. The etching solution used may be, for example, an aqueous solution of 10 mass % phosphoric acid, organic acid such as formic acid, acetic acid or citric acid, or sulfuric acid, or a chromate-phosphate mixture aqueous solution. For example, the etching is performed for 20 minutes using a phosphoric acid aqueous solution (10 mass %, 30° C.)

Then, the aluminum film 18 is again partially anodized such that the recessed portions 14p are grown in the depth direction and the thickness of the porous alumina layer 14 is increased as shown in FIG. 2A(d). Here, the growth of the recessed portions 14p starts at the bottoms of the previously-formed recessed portions 14p, and accordingly, the lateral surfaces of the recessed portions 14p have stepped shapes.

Thereafter, when necessary, the porous alumina layer 14 may be brought into contact with an alumina etchant to be further etched such that the pore diameter of the recessed portions 14p is further increased. The etching solution used in this step may preferably be the above-described etching solution. Practically, the same etching bath may be used.

In this way, by alternately repeating the anodization step and the etching step as described above through multiple cycles (e.g., 5 cycles: including 5 anodization cycles and 4 etching cycles), the moth-eye mold 100A that includes the porous alumina layer 14 which has the inverted moth-eye structure is obtained as shown in FIG. 2A(e). Since the process is ended with the anodization step, the recessed portions 14p have pointed bottom portion. That is, the resultant mold enables formation of raised portions with pointed tip ends.

The porous alumina layer 14 (thickness: $t_p$) shown in FIG. 2A(e) includes a porous layer (whose thickness is equivalent to the depth Dd of the recessed portions 14p) and a barrier layer (thickness: $t_b$). Since the porous alumina layer 14 has a structure obtained by inverting the moth-eye structure of the synthetic polymer film 34A, corresponding parameters which define the dimensions may sometimes be designated by the same symbols.

The recessed portions 14p of the porous alumina layer 14 may have, for example, a conical shape and may have a stepped lateral surface. It is preferred that the two-dimensional size of the recessed portions 14p (the diameter of a circle equivalent to the area of the recessed portions 14p when viewed in a normal direction of the surface), Dp, is more than 20 nm and less than 500 nm, and the depth of the recessed portions 14p, Dd, is not less than 50 nm and less than 1000 nm (1 µm). It is also preferred that the bottom portion of the recessed portions 14p is acute (with the deepest part of the bottom portion being pointed). When the recessed portions 14p are in a densely packed arrangement, assuming that the shape of the recessed portions 14p when viewed in a normal direction of the porous alumina layer 14 is a circle, adjacent circles overlap each other, and a saddle portion is formed between adjacent ones of the recessed portions 14p. Note that, when the generally-conical recessed portions 14p adjoin one another so as to form saddle portions, the two-dimensional size of the recessed portions 14p, Dp, is equal to the adjoining distance Dint. The thickness of the porous alumina layer 14, $t_p$, is not more than about 1 µm.

Under the porous alumina layer 14 shown in FIG. 2A(e), there is an aluminum remnant layer 18r. The aluminum remnant layer 18r is part of the aluminum film 18 which has not been anodized. When necessary, the aluminum film 18 may be substantially thoroughly anodized such that the aluminum remnant layer 18r is not present. For example, when the inorganic material layer 16 has a small thickness, it is possible to readily supply an electric current from the aluminum base 12 side.

The manufacturing method of the moth-eye mold illustrated herein enables manufacture of a mold which is for production of antireflection films disclosed in Patent Documents 2 to 4. Since an antireflection film used in a high-definition display panel is required to have high uniformity, selection of the material of the aluminum base, specular working of the aluminum base, and control of the purity and components of the aluminum film are preferably carried out as described above. However, the above-described mold manufacturing method can be simplified because the microbicidal activity can be achieved without high uniformity. For example, the surface of the aluminum base may be directly anodized. Even if, in this case, pits are formed due to impurities contained in the aluminum base, only local structural irregularities occur in the moth-eye structure of the finally-obtained synthetic polymer film 34A, and it is estimated that there is little adverse influence on the microbicidal activity.

According to the above-described mold manufacturing method, a mold in which the regularity of the arrangement of the recessed portions is low, and which is suitable to production of an antireflection film, can be manufactured. In the case of utilizing the microbicidal ability of the moth-eye structure, it is estimated that the regularity of the arrangement of the raised portions does not exert an influence. A mold for formation of a moth-eye structure which has regularly-arranged raised portions can be manufactured, for example, as described in the following section.

For example, after formation of a porous alumina layer having a thickness of about 10 µm, the formed porous alumina layer is removed by etching, and then, anodization may be performed under the conditions for formation of the above-described porous alumina layer. A 10 µm thick porous alumina layer is realized by extending the anodization duration. When such a relatively thick porous alumina layer is formed and then this porous alumina layer is removed, a porous alumina layer having regularly-arranged recessed portions can be formed without being influenced by irregularities which are attributed to grains that are present at the surface of an aluminum film or aluminum base or the process strain. Note that, in removal of the porous alumina layer, using a mixture solution of a chromate and a phosphate is preferred. Although continuing the etching for a long period of time sometimes causes galvanic corrosion, the mixture solution of a chromate and a phosphate has the effect of suppressing galvanic corrosion.

A moth-eye mold for production of the synthetic polymer film 34B shown in FIG. 1(b) can be, basically, manufactured by combination of the above-described anodization step and etching step. A manufacturing method of a moth-eye mold 100B that is for production of the synthetic polymer film 34B is described with reference to FIGS. 2B(a) to 2B(c).

Firstly, in the same way as illustrated with reference to FIGS. 2A(a) and 2A(b), the mold base 10 is provided, and the surface 18s of the aluminum film 18 is anodized, whereby a porous alumina layer 14 which has a plurality of recessed portions (micropores) 14p is formed.

Then, the porous alumina layer 14 is brought into contact with an alumina etchant such that a predetermined amount is etched away, whereby the opening of the recessed portions 14p is enlarged as shown in FIG. 2B(a). In this step, the etched amount is smaller than in the etching step illustrated with reference to FIG. 2A(c). That is, the size of the opening of the recessed portions 14p is decreased. For example, the etching is performed for 10 minutes using a phosphoric acid aqueous solution (10 mass %, 30° C.)

Then, the aluminum film 18 is again partially anodized such that the recessed portions 14p are grown in the depth direction and the thickness of the porous alumina layer 14 is increased as shown in FIG. 2B(b). In this step, the recessed portions 14p are grown deeper than in the anodization step illustrated with reference to FIG. 2A(d). For example, the anodization is carried out with an applied voltage of 80 V for 165 seconds (in FIG. 2A(d), 55 seconds) using an oxalic acid aqueous solution (concentration: 0.3 mass %, solution temperature: 10° C.).

Thereafter, the etching step and the anodization step are alternately repeated through multiple cycles in the same way as illustrated with reference to FIG. 2A(e). For example, 3 cycles of the etching step and 3 cycles of the anodization step are alternately repeated, whereby the moth-eye mold 100B including the porous alumina layer 14 which has the inverted moth-eye structure is obtained as shown in FIG. 2B(c). In this step, the two-dimensional size of the recessed portions 14p, Dp, is smaller than the adjoining distance Dint (Dp<Dint).

Figure 3:
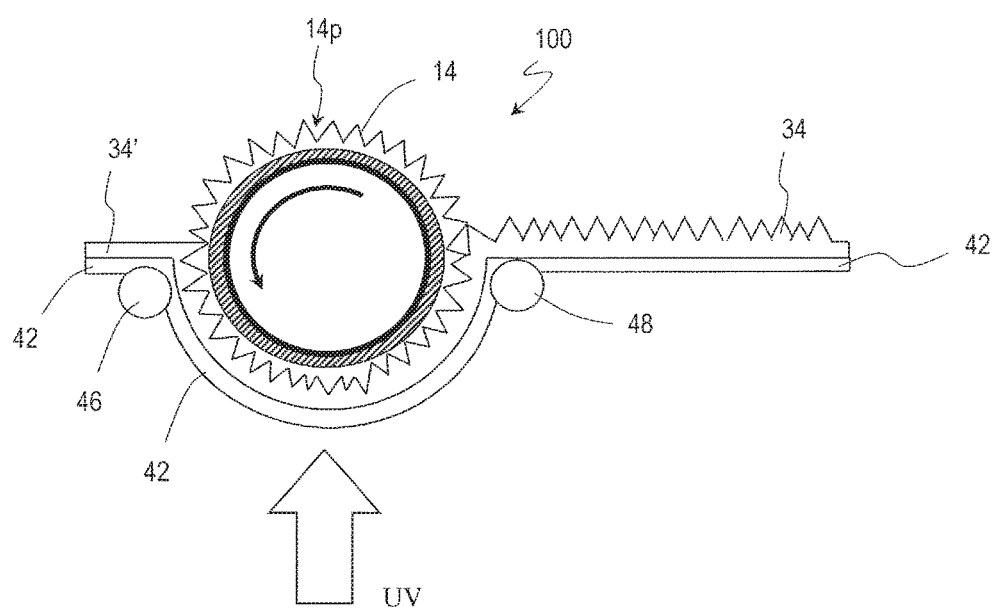
FIG. 3 A diagram for illustrating a method for producing a synthetic polymer film with the use of the moth-eye mold 100.

Next, a method for producing a synthetic polymer film with the use of a moth-eye mold 100 is described with reference to FIG. 3. FIG. 3 is a schematic cross-sectional view for illustrating a method for producing a synthetic polymer film according to a roll-to-roll method.

First, a moth-eye mold 100 in the shape of a hollow cylinder is provided. Note that the moth-eye mold 100 in the shape of a hollow cylinder is manufactured according to, for example, the manufacturing method described with reference to FIG. 2A.

As shown in FIG. 3, a base film 42 over which a UV-curable resin 34' is applied on its surface is maintained pressed against the moth-eye mold 100, and the UV-curable resin 34' is irradiated with ultraviolet (UV) light such that the UV-curable resin 34' is cured. The UV-curable resin 34' used may be, for example, an acrylic resin. The base film 42 may be, for example, a PET (polyethylene terephthalate) film or TAC (triacetyl cellulose) film. The base film 42 is fed from an unshown feeder roller, and thereafter, the UV-curable resin 34' is applied over the surface of the base film 42 using, for example, a slit coater or the like. The base film 42 is supported by supporting rollers 46 and 48 as shown in FIG. 3. The supporting rollers 46 and 48 have rotation mechanisms for carrying the base film 42. The moth-eye mold 100 in the shape of a hollow cylinder is rotated at a rotation speed corresponding to the carrying speed of the base film 42 in a direction indicated by the arrow in FIG. 3.

Thereafter, the moth-eye mold 100 is separated from the base film 42, whereby a synthetic polymer film 34 to which the inverted moth-eye structure of the moth-eye mold 100 is transferred is formed on the surface of the base film 42. The base film 42 which has the synthetic polymer film 34 formed on the surface is wound up by an unshown winding roller.

The surface of the synthetic polymer film 34 has the moth-eye structure obtained by inverting the surficial nanostructures of the moth-eye mold 100. According to the surficial nanostructure of the moth-eye mold 100 used, the synthetic polymer films 34A and 34B shown in FIGS. 1(a) and 1(b), respectively, can be produced. The material that forms the synthetic polymer film 34 is not limited to the UV-curable resin but may be a photocurable resin which is curable by visible light or may be a thermosetting resin.

Hereinafter, it is explained with experimental examples that the synthetic polymer film which has the above-described moth-eye structure over its surface has the microbicidal ability.

A mold manufactured according to the above-described mold manufacturing method was used to produce a synthetic polymer film having conical raised portions such as the raised portions 34Ap of the film 50A shown in FIG. 1(a). In sample films subjected to evaluation of the microbicidal activity, Dp was about 200 nm, Dint was about 200 nm, and Dh was about 150 nm (see FIG. 5, for example). From the viewpoint of causing local deformation of the cell wall, it is preferred that there is a large distance between adjoining raised portions. The difference between Dp and Dint is preferably, for example, 0 times to twice Dp, and more preferably 0.5 times to twice Dp. Here, Dp, Dint, and Dh represent the average values determined from SEM images. In photographing of the SEM images, a field emission scanning electron microscope (S-4700 manufactured by Hitachi, Ltd.) was used.

As the resin material used for formation of the synthetic polymer film, two types of UV-curable resins (Resin A and Resin B) were used. Resin A was a fluorine-containing acrylic resin. Resin B was a urethane acrylate-containing acrylic resin. A mold releasing agent was applied over the surfaces of respective synthetic polymer films, whereby synthetic polymer films were obtained which had different surface free energies. The mold releasing agent used was a fluoric mold releasing agent (OPTOOL DSX manufactured by DAIKIN INDUSTRIES, LTD). The mold releasing agent was sprayed over the entire surface of the synthetic polymer films and dried at room temperature in air.

The surface tension of the sample films was evaluated by measuring the contact angle of water and hexadecane at 22° C. with respect to the sample films using a contact angle meter (PCA-1 manufactured by Kyowa Interface Science Co., Ltd). The average value of five measurements of the contact angle is shown in Table 1.

TABLE 1

| No. | SYNTHETIC POLYMER RESIN LAYER (BASE FILM: PET) | CONTACT ANGLE OF WATER (°) | CONTACT ANGLE OF HEXADECANE (°) | MICROBICIDAL ABILITY |
|---|---|---|---|---|
| 1 | FLUORINE-CONTAINING ACRYLIC RESIN | 131.2 | 30.7 | ◯ |
| 2 | FLUORINE-CONTAINING ACRYLIC RESIN + MOLD RELEASING AGENT (0.1 mass %) | 126.2 | 50.9 | Δ |
| 3 | URETHANE ACRYLATE-CONTAINING ACRYLIC RESIN | 12.0 | 4.8 | ◯ |
| 4 | URETHANE ACRYLATE-CONTAINING ACRYLIC RESIN + MOLD RELEASING AGENT (0.01 mass %) | 73.3 | 9.4 | ◯ |

The microbicidal ability was evaluated through the following procedure:

1. Beads with frozen *P. aeruginosa* bacteria (purchased from National Institute of Technology and Evaluation) were immersed in a broth at 37° C. for 24 hours, whereby the *P. aeruginosa* bacteria were thawed;
2. Centrifugation (3000 rpm, 10 minutes);
3. The supernatant of the broth was removed;
4. Sterilized water was added, and the resultant solution was stirred and thereafter subjected to centrifugation again;
5. Steps 2 to 4 were repeated three times to obtain an undiluted bacterial solution (bacteria count: 1E+08 CFU/mL);

6. 1/500 NB culture medium and bacterial dilution A (bacteria count: 1E+06 CFU/mL) were prepared.

1/500 NB culture medium: NB culture medium (nutrient broth medium E-MC35 manufactured by Eiken Chemical Co., Ltd.) was diluted 500-fold with sterilized water.

Bacterial Dilution A: Undiluted Bacterial Solution 500 μL+Broth 100 μL+Sterilized Water 49.4 mL;

7. Bacterial dilution B was prepared by adding the 1/500 NB culture medium as a nutrient source to bacterial dilution A (in accordance with JIS Z2801 5.4a))

8. Bacterial dilution B was sprayed twice from a distance of about 10 cm on each of the sample films placed on a black acrylic plate (the amount of one spray: about 150 μL);

9. The sample films sprayed with bacterial dilution B are left in an airtight resin container (37° C., relative humidity 100%) for a predetermined time period;

10. Thereafter, the surfaces of the sample films were stamped with PETAN CHECK™ (product name: PT1025, manufactured by Eiken Chemical Co., Ltd.) such that the bacteria on the sample film surfaces were transferred to the standard agar medium;

11. The bacteria transferred to the standard agar medium were cultured at 37° C. for 24 hours, and thereafter, the presence/absence of colonies was checked.

In each of sample films No. 1 to No. 4, films left at Step 9 under the conditions that the time period was 0 hour (5 minutes) or 3 hours were subjected to PETAN CHECK™. The results of culturing at the standard agar medium are shown in FIGS. 4(a) and 4(b). In FIG. 4(a), the upper part shows the evaluation results of sample film No. 1 (the time period: 0 hour (5 minutes), 3 hours), and the lower part shows the evaluation results of sample film No. 2 (the time period: 0 hour (5 minutes), 3 hours). In FIG. 4(b), the upper part shows the evaluation results of sample film No. 3 (the time period: 0 hour (5 minutes), 3 hours), and the lower part shows the evaluation results of sample film No. 4 (the time period: 0 hour (5 minutes), 3 hours).

Refer to FIGS. 4(a) and 4(b). As for sample films No. 1 to No. 4, the samples on the left hand side (the time period was 0 hour (5 minutes)) show that grown bacteria covers the substantially entire surface of the medium, while in the samples on the right hand side of sample films Nos. 1, 3 and 4 (the time period was 3 hours), growth of the bacteria was not detected. In the sample on the right hand side of sample film No. 2 (the time period: 3 hours), growth of the bacteria was detected, but the number of grown bacteria was obviously smaller than in the sample on the left hand side (the time period: 0 hour (5 minutes)).

From the foregoing, it is understood that every one of sample films No. 1 to No. 4 has a microbicidal activity. One of the possible reasons that the microbicidal activity of sample film No. 2 is weaker than that of sample film No. 1 is the difference in surface free energy. As seen from Table 1, the contact angle of sample film No. 2 with respect to hexadecane is 50.9°, which is greater by about 20° than that of sample film No. 1 (30.7°). That is, it is inferred that the microbicidal ability of sample film No. 2 is weaker because the surface of sample film No. 2 has inferior lipophilicity to the surface of sample film No. 1.

FIGS. 5(a) to 5(d) show examples of SEM (Scanning Electron Microscope) observation of *P. aeruginosa* bacteria which died at a surface of sample film No. 1 which had a moth-eye structure. The full scale in the SEM images of FIGS. 5(a) and 5(b) is 1 μm. FIGS. 5(c) and 5(d) are enlarged views of FIGS. 5(a) and 5(b), respectively, in which the full scale in the SEM images is 500 nm.

As seen from these SEM images, the tip end portions of the raised portions enter the cell wall (exine) of a *P. aeruginosa* bacterium. In FIGS. 5(c) and 5(d), the raised portions do not appear to break through the cell wall but appears to be taken into the cell wall. This might be explained by the mechanism suggested in the "Supplemental Information" section of Non-patent Document 1. That is, it is estimated that the exine (lipid bilayer) of the Gram-negative bacteria came close to the raised portions and deformed so that the lipid bilayer locally underwent a transition like a first-order phase transition (spontaneous reorientation) and openings were formed in portions close to the raised portions, and the raised portions entered these openings.

Apart from the validity of the above-described mechanism, it is inferred from the above-described experimental results that when the surface of a synthetic polymer film has appropriate lipophilicity (preferably, the contact angle with respect to hexadecane is not more than 50.9°), the Gram-negative bacteria in the aqueous solution come close to the raised portions of the synthetic polymer film to cause interaction, and as a result, the raised portions enter the exine (lipid bilayer) of the Gram-negative bacteria so that the cell wall is broken. In this case, the force which acts on the exine of the Gram-negative bacteria depends on the free energy of the surface of the exine, the free energy of the surface of the raised portions, and the free energy of water which is in contact with these surfaces. It is estimated that, when the raised portions are lipophilic, the force which acts on the exine is large. As seen from the results of Table 1, the contact angle of the surface of the synthetic polymer film with respect to hexadecane is preferably not more than 51°, and more preferably not more than 31°. It can be said that, as the contact angle decreases, the microbicidal activity increases. Also as seen from the results of Table 1, the contact angle of the surface of the synthetic polymer film with respect to water ranges from 12.0° to 131.2°. It is understood that the hydrophilicity (or, conversely, hydrophobicity) of the surface of the synthetic polymer film which is evaluated by the contact angle of water does not directly relate to the microbicidal activity.

Next, the results of experiments for verifying the microbicidal activity achieved by the moth-eye structure of sample film No. 1 are described with reference to FIGS. 6(a) to 6(f). For comparison with sample film No. 1 that is a synthetic polymer film which has the moth-eye structure, a flat synthetic polymer film without the moth-eye structure which was made of the same resin material as sample film No. 1 (comparative example 1) and a PET film which is on the rear surface of sample film No. 1 (comparative example 2) were evaluated as to the microbicidal ability through the following procedure.

1. A 400 μL drop of the above-described bacterial dilution A (bacteria count: 1E+06 CFU/mL) was placed on each of the sample films. A cover (e.g., cover glass) was placed over the bacterial dilution A to adjust the amount of the bacterial dilution A per unit area (about 0.4 mL/cm$^2$).

Meanwhile, a sample without a cover over the bacterial dilution A was also prepared.

2. The samples were left in an environment where the temperature was 37° C. and the relative humidity was 100% for a predetermined time period. Thereafter, the entire sample film with the bacterial dilution A and 10 mL sterilized water were put into a filter bag.

3. The sample films were rubbed with hands over the filter bag to sufficiently wash away the bacteria from the sample films (post-wash solution (sometimes referred to as "bacterial dilution B'"), bacteria count: 1E+04 CFU/mL).

4. 1 mL of the post-wash solution was put into 9 mL phosphate buffer solution, whereby bacterial dilution C (bacteria count: 1E+03 CFU/mL) was prepared.

5. 1 mL of the bacterial dilution C was put into 9 mL phosphate buffer solution, whereby bacterial dilution D (bacteria count: 1E+02 CFU/mL) was prepared. Then, 1 mL of the bacterial dilution D was put into 9 mL phosphate buffer solution, whereby bacterial dilution E (bacteria count: 1E+01 CFU/mL) was prepared.

6. 1 mL drops of the bacterial dilutions C to E were placed on Petrifilm™ media (product name: Aerobic Count Plate (AC), manufactured by 3M). The bacteria were cultured at 37° C. with the relative humidity of 100%. After 48 hours, the number of bacteria in the bacterial dilution B' was counted.

The results are shown in Table 2 below. FIG. 6(a) shows the state of sample film No. 1 with a cover. FIG. 6(b) shows the state of a sample of comparative example 1 with a cover. FIG. 6(c) shows the state of a sample of comparative example 2 with a cover. FIG. 6(d) shows the state of sample film No. 1 without a cover. FIG. 6(e) shows the state of a sample of comparative example 1 without a cover. FIG. 6(f) shows the state of a sample of comparative example 2 without a cover.

TABLE 2

|  | SAMPLE FILM NO. 1 | COMPARATIVE EXAMPLE 1 | COMPARATIVE EXAMPLE 2 |
| --- | --- | --- | --- |
| WITH COVER | 0 | 7.10E+05 | 1.14E+06 |
| WITHOUT COVER | 2.73E+05 | 2.50E+05 | 8.10E+05 |

As clearly seen from the results of Table 2, only sample film No. 1 produced the microbicidal activity. The microbicidal activity was produced by the moth-eye structure irrespective of the type of the resin material that forms the synthetic polymer film.

Note that sample film No. 1 did not produce the microbicidal activity when the cover was not placed over the bacterial dilution. This is probably because a large number of bacteria were not killed at the surface which had the moth-eye structure, and these bacteria grew.

A synthetic polymer film according to an embodiment of the present invention is suitably applicable to uses of suppressing generation of slime on a surface which is in contact with water, for example. For example, the synthetic polymer film is attached onto the inner walls of a water container for a humidifier or ice machine, whereby generation of slime on the inner walls of the container can be suppressed. The slime is attributed to a biofilm which is formed of extracellular polysaccharide (EPS) secreted from bacteria adhering to the inner walls and the like. Therefore, killing the bacteria adhering to the inner walls and the like enables suppression of generation of the slime.

As described above, bringing a liquid into contact with the surface of a synthetic polymer film according to an embodiment of the present invention enables sterilization of the liquid. Likewise, bringing a gas into contact with the surface of a synthetic polymer film according to an embodiment of the present invention enables sterilization of the gas. In general, microorganisms have such a surface structure that they can easy adhere to the surface of an object in order to increase the probability of contact with organic substances which will be their nutrients. Therefore, when a liquid or gas which contains microorganisms is brought into contact with a microbicidal surface of a synthetic polymer film according to an embodiment of the present invention, the microorganisms are likely to adhere to the surface of the synthetic polymer film, and therefore, on that occasion, the liquid or gas is subjected to the microbicidal activity.

Although the microbicidal activity of a synthetic polymer film according to an embodiment of the present invention against *P. aeruginosa* that is a Gram-negative bacteria has been described in this section, the synthetic polymer film has a microbicidal activity not only on Gram-negative bacteria but also on Gram-positive bacteria and other microorganisms. One of the characteristics of the Gram-negative bacteria resides in that they have a cell wall including an exine. The Gram-positive bacteria and other microorganisms (including ones that do not have a cell wall) have a cell membrane. The cell membrane is formed by a lipid bilayer as is the exine of the Gram-negative bacteria. Therefore, it is estimated that the interaction between the raised portions of the surface of the synthetic polymer film according to an embodiment of the present invention and the cell membrane is basically the same as the interaction between the raised portions and the exine.

Note that, however, the size of the microorganisms varies depending on their types. The size of *P. aeruginosa* which has been described herein as an example is about 1 μm. However, the size of the bacteria ranges from several hundreds of nanometers to about five micrometers. The size of fungi is not less than several micrometers. It is estimated that the raised portions of the synthetic polymer film which has been described above (the two-dimensional size is about 200 nm) have a microbicidal activity on a microorganism whose size is not less than about 0.5 μm, but there is a probability that the raised portions are too large to exhibit a sufficient microbicidal activity on a bacterium whose size is several hundreds of nanometers. The size of viruses ranges from several tens of nanometers to several hundreds of nanometers, and many of them have a size of not more than 100 nm. Note that viruses do not have a cell membrane but have a protein shell called capsid which encloses virus nucleic acids. It is estimated that the raised portions likewise act on this shell.

In view of the above, the configuration and production method of a synthetic polymer film having raised portions which can exhibit a microbicidal activity against a microorganism of not more than several hundreds of nanometers are described below.

In the following description, raised portions of the above-described synthetic polymer film which have a two-dimensional size in the range of more than 20 nm and less than 500 nm are referred to as "first raised portions". Raised portions which are superimposedly formed over the first raised portions are referred to as "second raised portions". The two-dimensional size of the second raised portions is smaller than the two-dimensional size of the first raised portions and does not exceed 100 nm. Note that when the two-dimensional size of the first raised portions is less than 100 nm, particularly less than 50 nm, it is not necessary to provide the second raised portions. Recessed portions of the mold corresponding to the first raised portions are referred to as "first recessed portions", and recessed portions of the mold corresponding to the second raised portions are referred to as "second recessed portions".

When the method of forming the first recessed portions which have predetermined size and shape by alternately performing the anodization step and the etching step as described above is applied without any modification, the second recessed portions cannot be formed successfully.

FIG. 7(a) shows a SEM image of a surface of an aluminum base (designated by reference numeral 12 in FIG. 2A). FIG. 7(b) shows a SEM image of a surface of an aluminum film (designated by reference numeral 18 in FIG. 2A). FIG. 7(c) shows a SEM image of a cross section of the aluminum film (designated by reference numeral 18 in FIG. 2A). As seen from these SEM images, there are grains (crystal grains) at the surface of the aluminum base and the surface of the aluminum film. The grains of the aluminum film form unevenness at the surface of the aluminum film. This unevenness at the surface affects formation of the recessed portions in the anodization and therefore interrupts formation of second recessed portions whose Dp or Dint is smaller than 100 nm.

In view of the above, a mold manufacturing method according to an embodiment of the present invention includes: (a) providing an aluminum base or an aluminum film deposited on a support; (b) the anodization step of applying a voltage at the first level while a surface of the aluminum base or aluminum film is kept in contact with an electrolytic solution, thereby forming a porous alumina layer which has the first recessed portions; (c) after step (b), the etching step of bringing the porous alumina layer into contact with an etching solution, thereby enlarging the first recessed portions; and (d) after step (c), applying a voltage at the second level that is lower than the first level while the porous alumina layer is kept in contact with an electrolytic solution, thereby forming the second recessed portions in the first recessed portions. For example, the first level is higher than 40 V, and the second level is equal to or lower than 20 V.

Specifically, an anodization step is carried out with the voltage at the first level, whereby the first recessed portions are formed which have such a size that is not influenced by the grains of the aluminum base or aluminum film. Thereafter, the thickness of the barrier layer is decreased by etching, and then, another anodization step is carried out with the voltage at the second level that is lower than the first level, whereby the second recessed portions are formed in the first recessed portions. When the second recessed portions are formed through such a procedure, the influence of the grains is avoided.

Figure 8:
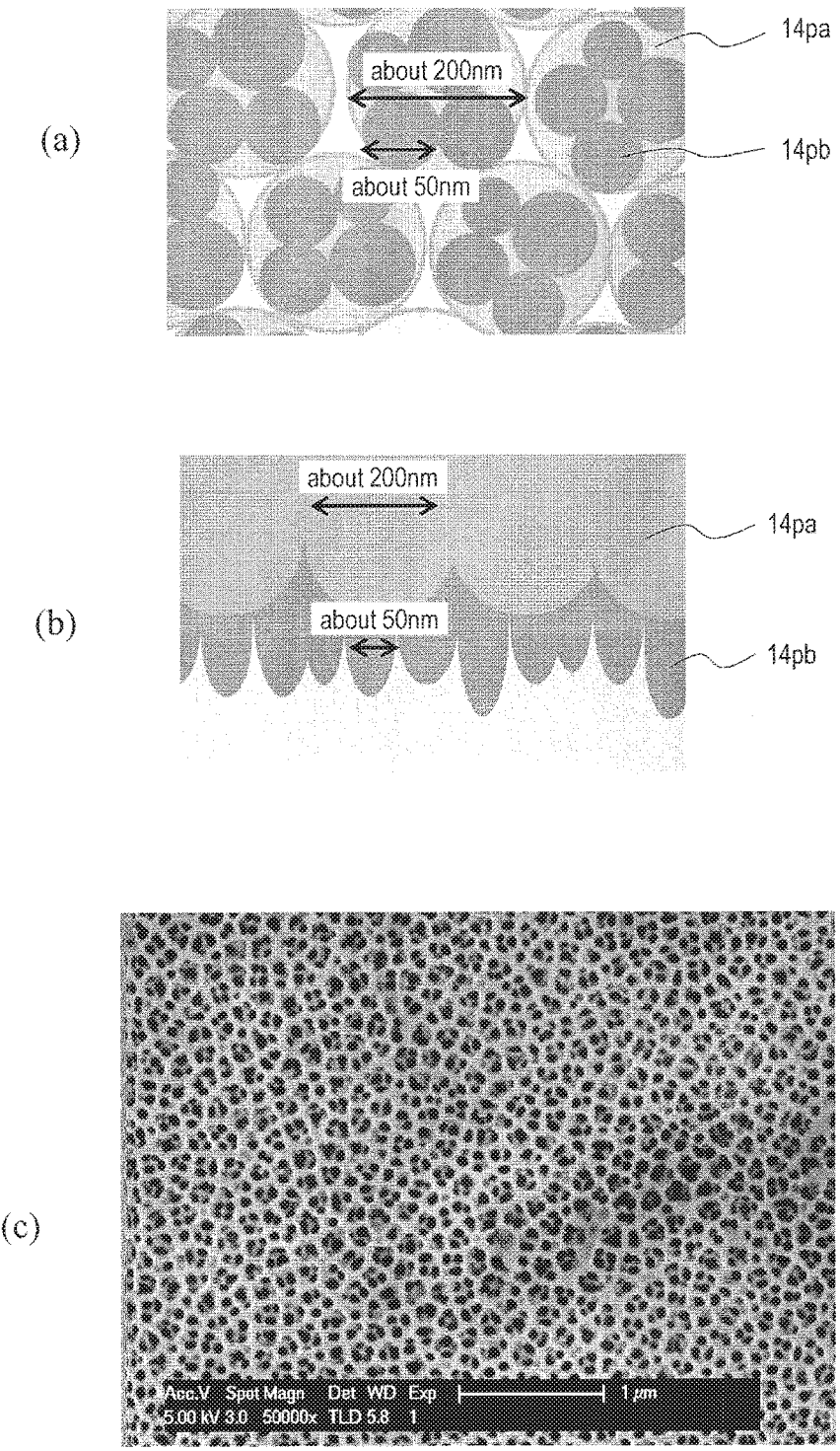
FIG. 8 (a) is a schematic plan view of a porous alumina layer of a mold. (b) is a schematic cross-sectional view of the porous alumina layer. (c) is a SEM image of a prototype mold.
Figure 9:
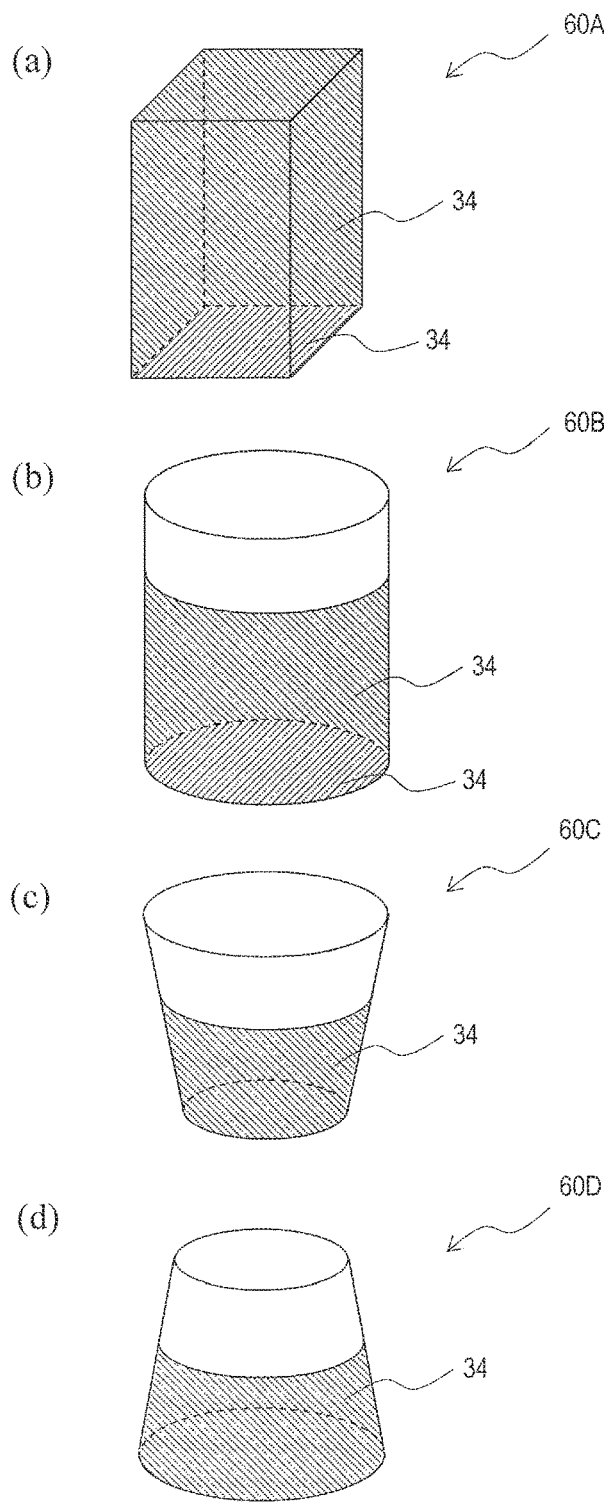
FIG. 9 (a) to (d) are schematic perspective views showing containers according to an embodiment of the present invention.
Figure 10:
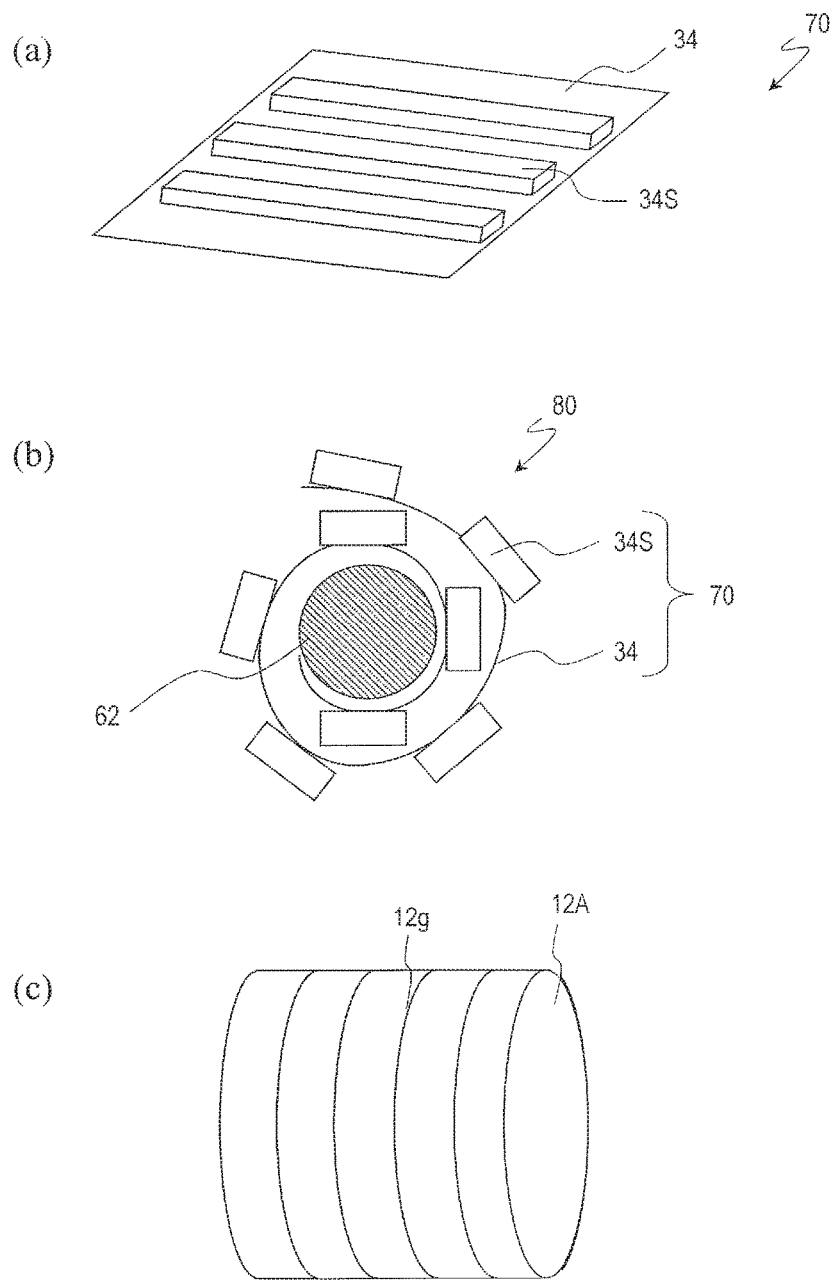
FIG. 10 (a) is a schematic diagram showing a film for use in a sterilization filter according to an embodiment of the present invention. (b) is a schematic diagram showing a sterilization filter. (c) is a schematic diagram showing an aluminum base for use in a mold that is for production of a film.
Figure 11:
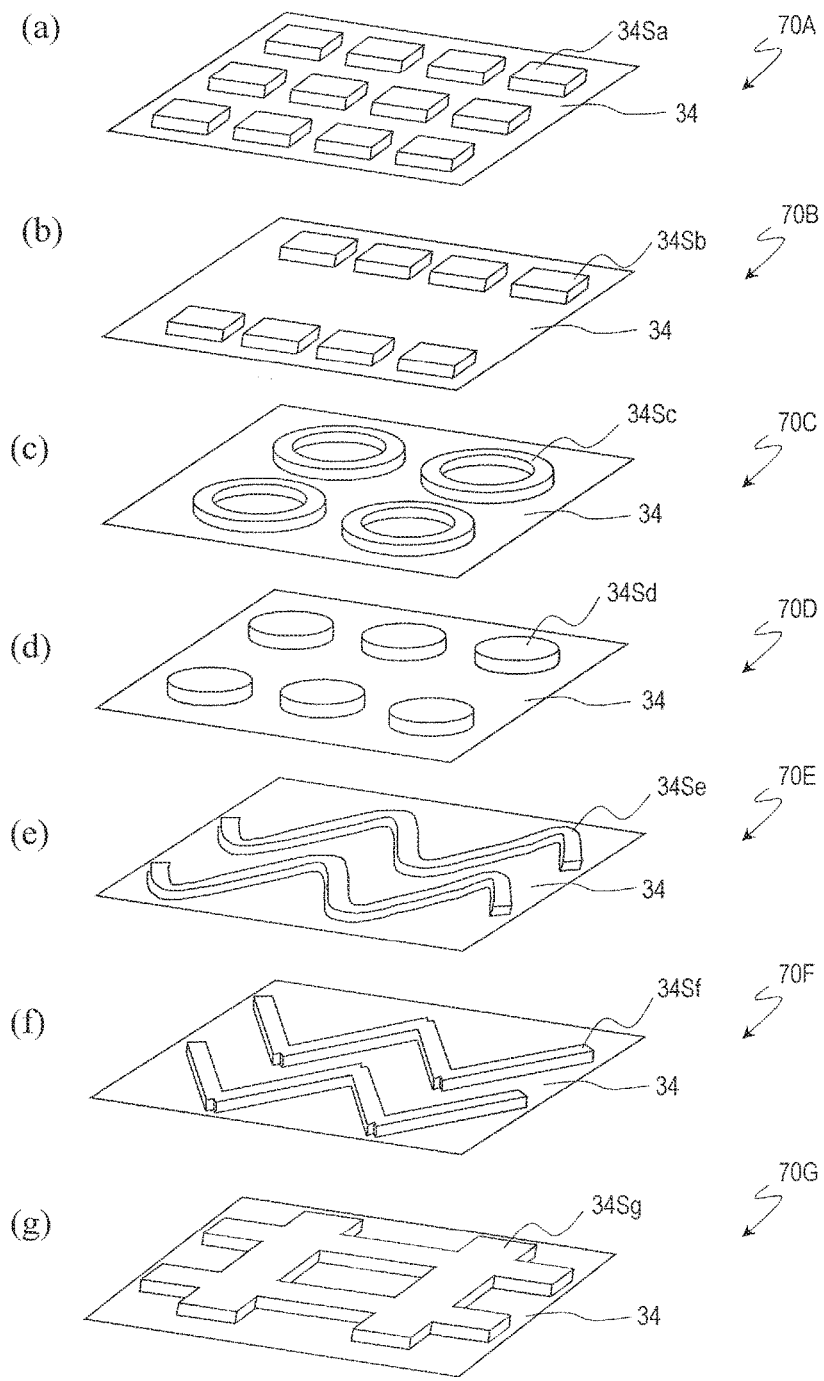
FIG. 11 (a) to (g) are schematic diagrams showing other films for use in a sterilization filter according to an embodiment of the present invention.

A mold which has first recessed portions 14pa and second recessed portions 14pb formed in the first recessed portions 14pa is described with reference to FIG. 8. FIG. 8(a) is a schematic plan view of a porous alumina layer of a mold. FIG. 8(b) is a schematic cross-sectional view of the porous alumina layer. FIG. 8(c) shows a SEM image of a prototype mold.

As shown in FIGS. 8(a) and 8(b), the surface of the mold of the present embodiment has the plurality of first recessed portions 14pa whose two-dimensional size is in the range of more than 20 nm and less than 500 μm and the plurality of second recessed portions 14pb which are superimposedly formed over the plurality of first recessed portions 14pa. The two-dimensional size of the plurality of second recessed portions 14pb is smaller than the two-dimensional size of the plurality of first recessed portions 14pa and does not exceed 100 nm. The height of the second recessed portions 14pb is, for example, more than 20 nm and not more than 100 nm. The second recessed portions 14pb preferably have a generally conical portion as do the first recessed portions 14pa.

The porous alumina layer shown in FIG. 8(c) was formed as described below.

The aluminum film used was an aluminum film which contains Ti at 1 mass %. The anodization solution used was an oxalic acid aqueous solution (concentration: 0.3 mass %, solution temperature: 10° C.). The etching solution used was a phosphoric acid aqueous solution (concentration: 10 mass %, solution temperature: 30° C.). After the anodization was carried out with a voltage of 80 V for 52 seconds, the etching was carried out for 25 minutes. Then, the anodization was carried out with a voltage of 80 V for 52 seconds, and the etching was carried out for 25 minutes. Thereafter, the anodization was carried out with a voltage of 20 V for 52 seconds, and the etching was carried out for 5 minutes. Further, the anodization was carried out with a voltage of 20 V for 52 seconds.

As seen from FIG. 8(c), the second recessed portions whose Dp was about 50 nm were formed in the first recessed portions whose Dp was about 200 nm. When in the above-described manufacturing method the voltage at the first level was changed from 80 V to 45 V for formation of the porous alumina layer, the second recessed portions whose Dp was about 50 nm were formed in the first recessed portions whose Dp was about 100 nm.

When a synthetic polymer film is produced using such a mold, the produced synthetic polymer film has raised portions whose configuration is the inverse of that of the first recessed portions 14pa and the second recessed portions 14pb shown in FIGS. 8(a) and 8(b). That is, the produced synthetic polymer film further includes a plurality of second raised portions superimposedly formed over a plurality of first raised portions.

The thus-produced synthetic polymer film which has the first raised portions and the second raised portions superimposedly formed over the first raised portions has a microbicidal activity on various microorganisms, ranging from relatively small microorganisms of about 100 nm to relatively large microorganisms of not less than 5 μm.

As a matter of course, only raised portions whose two-dimensional size is in the range of more than 20 nm and less than 100 nm may be formed according to the size of a target microorganism. The mold for formation of such raised portions can be manufactured, for example, as described below.

The anodization is carried out using a neutral salt aqueous solution (ammonium borate, ammonium citrate, etc.), such as an ammonium tartrate aqueous solution, or an organic acid which has a low ionic dissociation degree (maleic acid, malonic acid, phthalic acid, citric acid, tartaric acid, etc.) to form a barrier type anodized film. After the barrier type anodized film is removed by etching, the anodization is carried out with a predetermined voltage (the voltage at the second level described above), whereby recessed portions whose two-dimensional size is in the range of more than 20 nm and less than 100 nm can be formed.

For example, an aluminum film which contains Ti at 1 mass % is anodized at 100 V for 2 minutes using a tartaric acid aqueous solution (concentration: 0.1 mol/l, solution temperature: 23° C.), whereby a barrier type anodized film is formed. Thereafter, the etching is carried out for 25 minutes using a phosphoric acid aqueous solution (concentration: 10 mass %, solution temperature: 30° C.), whereby the barrier type anodized film is removed. Thereafter, the anodization and the etching are alternatively repeated as described above, specifically through 5 anodization cycles and 4 etching cycles. The anodization was carried out at 20 V for 52 seconds using an oxalic acid aqueous solution (concentration: 0.3 mass %, solution temperature: 10° C.) as the anodization solution. The etching was carried out for 5 minutes using the above-described etching solution. As a result, recessed portions whose two-dimensional size is about 50 nm can be uniformly formed.

Next, application examples of the above-described synthetic polymer film whose surface has a microbicidal activity are described with reference to FIG. 9 to FIG. 14.

FIGS. 9(a) to 9(d) are schematic perspective views showing containers according to an embodiment of the present invention. The containers 60A to 60D shown in FIGS. 9(a) to 9(d) are, for example, a container for containing water. These containers have the above-described synthetic polymer film 34 whose surface has a microbicidal activity (i.e., surface has the moth-eye structure) in at least part of the inner walls. The synthetic polymer film 34 has over its surface a plurality of first raised portions whose two-dimensional size viewed in a direction normal to the surface is more than 20 nm and less than 500 nm. The first raised portions are, for example, the raised portions 34Ap shown in FIG. 1(a) or the raised portions 34Bp shown in FIG. 1(b). The synthetic polymer film 34 may further have a plurality of second raised portions superimposedly formed over the plurality of first raised portions. The two-dimensional size of the plurality of second raised portions is smaller than the two-dimensional size of the plurality of first raised portions and does not exceed 100 nm.

In the container 60A shown in FIG. 9(a), the inner walls and bottom wall of the container are substantially entirely covered with the synthetic polymer film 34. As in the container 60B shown in FIG. 9(b), only part of the inner walls of the container may be covered with the synthetic polymer film 34. Alternatively, it is possible to adopt a configuration where the synthetic polymer film 34 is not provided in the bottom surface, such as the container 60C shown in FIG. 9(c) and the container 60D shown in FIG. 9(d).

These containers 60A to 60D can be used as, for example, a container for water used in a humidifier or ice machine. The main body of the containers 60A to 60D is made of, for example, plastic but may be made of any other material (metal or inorganic material). The shape of the containers is not limited to illustrated examples but may be any shape. By adhering the synthetic polymer film 34 to at least the inner walls of the container, generation of slime on the inner walls of the container can be suppressed. Since the slime is attributed to a biofilm which is formed of extracellular polysaccharide (EPS) secreted from bacteria adhering to the inner walls and the like, killing the bacteria adhering to the inner walls and the like enables suppression of generation of the slime. Since bacteria are likely to multiply near the boundary between water and air, it is preferred to provide the synthetic polymer film 34 in at least such a region of the inner walls.

A sterilization filter according to an embodiment of the present invention utilizes the microbicidal activity of a surface of the synthetic polymer film 34 which has the moth-eye structure. Therefore, it is preferred that the total area per unit volume of the surface that has the microbicidal activity is large. To this end, in the filter, the synthetic polymer film 34 is arranged in a predetermined shape, and in that arrangement of the shape, the inclination of the normal to the surface of the synthetic polymer film 34 which has the moth-eye structure varies depending on its position over the surface, and the inclination of the normal to a surface opposite to the surface that has the moth-eye structure varies depending on its position over the opposite surface. That is, the synthetic polymer film 34 is, for example, bent or folded. The synthetic polymer film 34 is configured such that at least part of the surface that has the moth-eye structure is capable of coming into contact with a gas or liquid. The filter may have a plurality of synthetic polymer films 34 such that the plurality of synthetic polymer films 34 are stacked up together. Also in this case, the plurality of synthetic polymer films 34 may be bent or folded. The filter may further have a plurality of synthetic polymer film pieces whose surface has the moth-eye structure. A sterilization filter according to an embodiment of the present invention is not limited to examples illustrated below but may have any shape and/or configuration.

FIG. 10(a) shows a schematic diagram of a film 70 for use in a sterilization filter according to an embodiment of the present invention. The synthetic polymer film 34 included in the film 70 has a plurality of spacer portions 34S on the surface that has the moth-eye structure. The film 70 has a base film (not shown) such as the base films 42A, 42B of the films 50A, 50B shown in FIGS. 1(a) and 1(b), for example.

The film 70 is in a spiral arrangement around a bar 62 as shown in FIG. 10(b) to form a sterilization filter 80. That is, in the sterilization filter 80, a cross section of the film 70 forms a spiral. Note that the sterilization filter 80 may include any other member than the film 70. For example, the sterilization filter 80 may include a holding member (case) for keeping the film 70 in a predetermined shape.

The spacer portions 34S of the film 70 prevent the rear surface of the film 70 in a spiral arrangement from coming into close contact with, or being in the vicinity of, the surface of the synthetic polymer film 34 which has the moth-eye structure, and form a space above the moth-eye structure. This space constitutes a path of a liquid or gas, thereby increasing the probability that microorganisms come into contact with the moth-eye structure of the synthetic polymer film 34. The plurality of spacer portions 34S are, for example, rectangular parallelepipeds extending parallel to one another as shown in FIG. 10(a). The height (the height in a direction normal to the film) of the spacer portions 34S is, for example, not less than 1 μm, and is appropriately set. The width of the spacer portions 34S is, for example, not less than 1 mm, and is appropriately set.

Although in the example described here the film 70 is in a spiral arrangement, a plurality of annular films 70 (e.g., in the form of a hollow cylinder or square tube) may be arranged concentrically. In this case, a cross section of the film 70 forms at least one ring (circle). In such an arrangement that a cross section of the film 70 (i.e., the synthetic polymer film 34) forms a spiral or ring, the surface that has the moth-eye structure is oriented in all directions and therefore exhibits a microbicidal activity against a microorganism approaching in an arbitrary direction. Note that the film 70 may have a through hole so as to form a flow which includes a component of a direction perpendicular to the film surface of the film 70.

The synthetic polymer film 34 that has the spacer portions 34S can be produced using a moth-eye mold that is manufactured according to the manufacturing method previously described with reference to FIG. 2, for example, with the use of an aluminum base 12A which has grooves 12g corresponding to the spacer portions 34S as shown in FIG. 10(c). The method for forming the grooves 12g in the aluminum base 12 is, for example, bite cutting.

The shape and arrangement of the spacer portions 34S can be changed variously. For example, spacer portions 34Sa to 34Sg of films 70A to 70G shown in FIGS. 11(a) to 11(g) may be provided.

As in the film 70A shown in FIG. 11(a), spacer portions 34Sa in the form of rectangular parallelepiped pillars (in the form of dots) may be arranged in a matrix. Alternatively, as in the film 70B shown in FIG. 11(b), spacer portions 34Sb in the form of rectangular parallelepiped pillars may be arranged in a broken line arrangement. The shape of the pillar-like spacers is not particularly limited. For example, they may be in the shape of a ring, such as spacer portions 34Sc of the film 70C shown in FIG. 11(c). Alternatively, they may be in the shape of a disk, such as spacer portions 34Sd of the film 70D shown in FIG. 11(d). Still alternatively, they may be polygonal or in any arbitrary shape.

As in the film 70E shown in FIG. 11(e), they may be corrugated spacer portions 34Se. Alternatively, as in the film 70F shown in FIG. 11(f), they may be zigzag spacer portions 34Sf. Still alternatively, as in the film 70G shown in FIG. 11(g), a spacer portion 34Sg may have the shape of a lattice.

The above-described spacer portions 34Sa to 34Sg can be realized by forming recessed portions corresponding to the spacer portions 34Sa to 34Sg in the surface of an aluminum base used in a mold that is for formation of the synthetic polymer film 34, in the same way as for the spacer portions 34S shown in FIG. 10(a). The spacers in the form of pillars (dots) which do not have regularity in shape and arrangement can also be formed by satin-finishing the surface of the aluminum base. The satin finishing may be realized by a mechanical process, such as a sandblaster method, or a chemical process, or may be realized by a combination of mechanical and chemical processes. The chemical satin finishing can be realized by using, for example, an ammonium hydrogen fluoride aqueous solution or ammonium fluoride aqueous solution. For example, the aluminum base is treated at 25° C. for 15 minutes with a mixture solution consisting of 1.67% ammonium fluoride, 0.67% ammonium sulfate, 0.67% ammonium dihydrogen phosphate, and water which constitutes the remaining part, whereby recessed portions which have such a depth that the surface roughness is not less than 1 μm can be formed.

Although in the above-described examples the spacer portions 34S are formed as part of the synthetic polymer film 34, the spacer portions 34S may be formed separately from the synthetic polymer film 34. Spacer portions which are formed separately from the synthetic polymer film 34 are herein referred to as "spacers". Note that the spacer portions and the spacers are designated by the same reference numeral. That is, the above-described spacer portions 34S may be formed as spacers 34S which are formed separately from the synthetic polymer film 34.

There can be various procedures for forming the spacers 34S separately from the synthetic polymer film 34. For example, after formation of the synthetic polymer film 34 that has the moth-eye structure, the spacers 34 can be formed in an arbitrary pattern on the surface of the synthetic polymer film 34 by, for example, screen printing or the like. Note that the spacer portions 34 or the spacers 34 preferably have a smaller area because a region in which the spacer portions 34 or the spacers 34 are provided does not have a microbicidal activity. Therefore, it is preferred that spacer portions or spacers in the form of pillars, such as the spacer portions 34Sa to 34Sd shown in FIGS. 11(a) to 11(d), are discretely arranged.

As a matter of course, the spacers are not necessarily required to be formed on the synthetic polymer film 34. The spacers may be arranged as separate (detachable or movable) parts such that a surface of the synthetic polymer film 34 which has the moth-eye structure is prevented from coming into contact with the other portions of the synthetic polymer film 34 or with any other member. Examples of such spacers include plastic pieces and threads of various shapes.

FIGS. 12(a) and 12(b) show schematic diagrams of other sterilization filters 80A and 80B according to an embodiment of the present invention.

The sterilization filter 80A shown in FIG. 12(a) has such a configuration that a film 72A is folded like bellows, and the film 72A includes the synthetic polymer films 34 on both sides of the base film (not shown). The sterilization filter 80A may include any other member than the film 72A, e.g., a holding member (case) for keeping the film 72A folded like bellows. By keeping the film 72A folded as in the sterilization filter 80A, a space for enabling a liquid or gas to come into contact with the surface of the synthetic polymer film 34 can be secured even if the spacers (spacer portions) are omitted.

The sterilization filter 80B shown in FIG. 12(b) includes a film 72B which is folded like bellows and which has the synthetic polymer film 34. The creases of the film 72B are fixed by an adhesive agent. Cotton threads 64, for example, are hung at the creases. The creases are fixed with tension F being kept on the cotton threads 64. Due to tension F on the cotton threads 64, the space between adjoining synthetic polymer films 34 is maintained. As a matter of course, wires, fishlines, or piano wires may be used instead of the cotton threads. Bars may be used instead of the threads.

The sterilization filters 80A and 80B have a relatively large space at the surface of the synthetic polymer film 34 and therefore can be suitably used as a filter for air cleaners, for example. By allowing air to efficiently flow through the large space secured at the surface of the synthetic polymer film 34, it is possible to efficiently sterilize microorganisms in the air.

FIGS. 13(a) to 13(c) show schematic diagrams of still another sterilization filter according to an embodiment of the present invention.

A sterilization filter 80C shown in FIG. 13(a) has a film 50 which includes a synthetic polymer film 34 that is fixed in the form of a hollow cylinder. By allowing a liquid or gas to pass through the space inside the hollow cylinder, it is possible to efficiently sterilize microorganisms in the liquid or gas. As a matter of course, another synthetic polymer film 34 may be provided on the outer surface of the hollow cylinder. The diameter of the hollow cylinder is, for example, not less than 1 mm.

As in a sterilization filter 80D shown in FIG. 13(b), a plurality of films 50 in the form of hollow cylinders may be bound together. Alternatively, as in a sterilization filter 80E shown in FIG. 13(c), a plurality of films 50 in the form of hollow cylinders may be placed in another hollow cylinder 82. These sterilization filters 80C to 80E can be used as a tubular sterilization filter.

FIG. 14(a) shows a schematic diagram of a sterilization filter 90A which utilizes electrophoresis according to an embodiment of the present invention. FIG. 14(b) shows a schematic diagram of a microbicidal container 90B which utilizes electrophoresis according to the present embodiment.

The sterilization filter 90A includes a film 70 processed in the shape of a hollow cylinder, the film 70 having a synthetic polymer film 34 at least on the inner perimeter surface, and a tubular member 92 placed inside the hollow cylindrical film 70 so as to be away from the cylindrical film 70. Here, the film 70 processed in the shape of a hollow cylinder and the hollow cylindrical member 92 are illustrated, although these components are not limited to particular shapes. A film processed in the shape of a tube whose cross-sectional shape is polygonal or oval can be used instead of the hollow cylindrical film 70. A solid cylindrical member may be used instead of the hollow cylindrical member 92. The cross-sectional shape may be polygonal or oval. Note that, however, using the hollow cylindrical member 92 or the solid cylindrical member 92 provides such an advantage that the distance r between the outer perimeter surface of the cylindrical member 92 and the inner perimeter surface of the hollow cylindrical film 70 is constant. The distance r can be appropriately adjusted such that a liquid can flow through the space between the film 70 and the hollow cylindrical member 92. For example, the distance r is not less than 1 mm.

The inner perimeter surface of the hollow cylindrical film 70 is a surface of the synthetic polymer film 34 which has the moth-eye structure and is supplied with a positive voltage from a DC power supply 95. The outer perimeter surface of the hollow cylindrical member 92 is supplied with a negative voltage from the DC power supply 95. Many of microorganisms m are negatively charged and therefore attracted to a surface of the synthetic polymer film 34 that is supplied with the positive voltage. On the other hand, many of proteins p are positively charged and therefore attracted to the outer perimeter surface of the hollow cylindrical member 92. Cations of sodium and the like are also attracted to the outer perimeter surface of the hollow cylindrical member 92. That is, negatively-charged microorganisms m are attracted to the surface of the synthetic polymer film 34 by electrophoresis and more efficiently undergo the microbicidal activity. On the other hand, positively-charged proteins p and sodium ions are attracted to the outer perimeter surface of the hollow cylindrical member 92 in the opposite direction to the microorganisms m, so that the microorganisms m are moved away from nutrients, and growth of the microorganisms m is suppressed. The outer perimeter surface of the hollow cylindrical member 92 may have, or may not have, the moth-eye structure.

To supply a positive voltage to a surface of the synthetic polymer film 34 which has the moth-eye structure, for example, an electrode 94p is formed on the surface of the synthetic polymer film 34. The electrode 94p can be formed by, for example, depositing an ITO thin film. Alternatively, electrical conductivity may be provided to the synthetic polymer film 34 so as to be used as the electrode 94p. The outer perimeter surface of the hollow cylindrical film 70 may also be provided with the synthetic polymer film 34. A surface of this synthetic polymer film 34 which has the moth-eye structure is also supplied with the positive voltage in the same way as that described above. To supply a negative voltage to the outer perimeter surface of the hollow cylindrical member 92, for example, an electrode 94n is provided.

The sterilization filter 90A is placed in, for example, a water storage tank. The sterilization filter 90A is preferably constructed in a cartridge configuration, for example, such that it can be easily replaced. The cartridge may include, for example, a plurality of sterilization filters 90A. When necessary, only the hollow cylindrical member 92 can be replaced.

The film 70 may have, for example, a base film as shown in FIG. 1. Electrical conductivity may be provided to the film 70. For example, an ITO layer, for example, may be provided between the base film and the synthetic polymer film. Alternatively, the film 70 may be provided on a surface of a cylinder which is made of a metal. Further, a metal layer whose zeta potential is positive in water may be provided on the surface of the synthetic polymer film 34 which has the moth-eye structure. When such a configuration is adopted, microorganisms can be attracted to the surface of the synthetic polymer film 34 which has the moth-eye structure without application of a voltage from an external device, so that the power consumption can be reduced.

Figure 13:
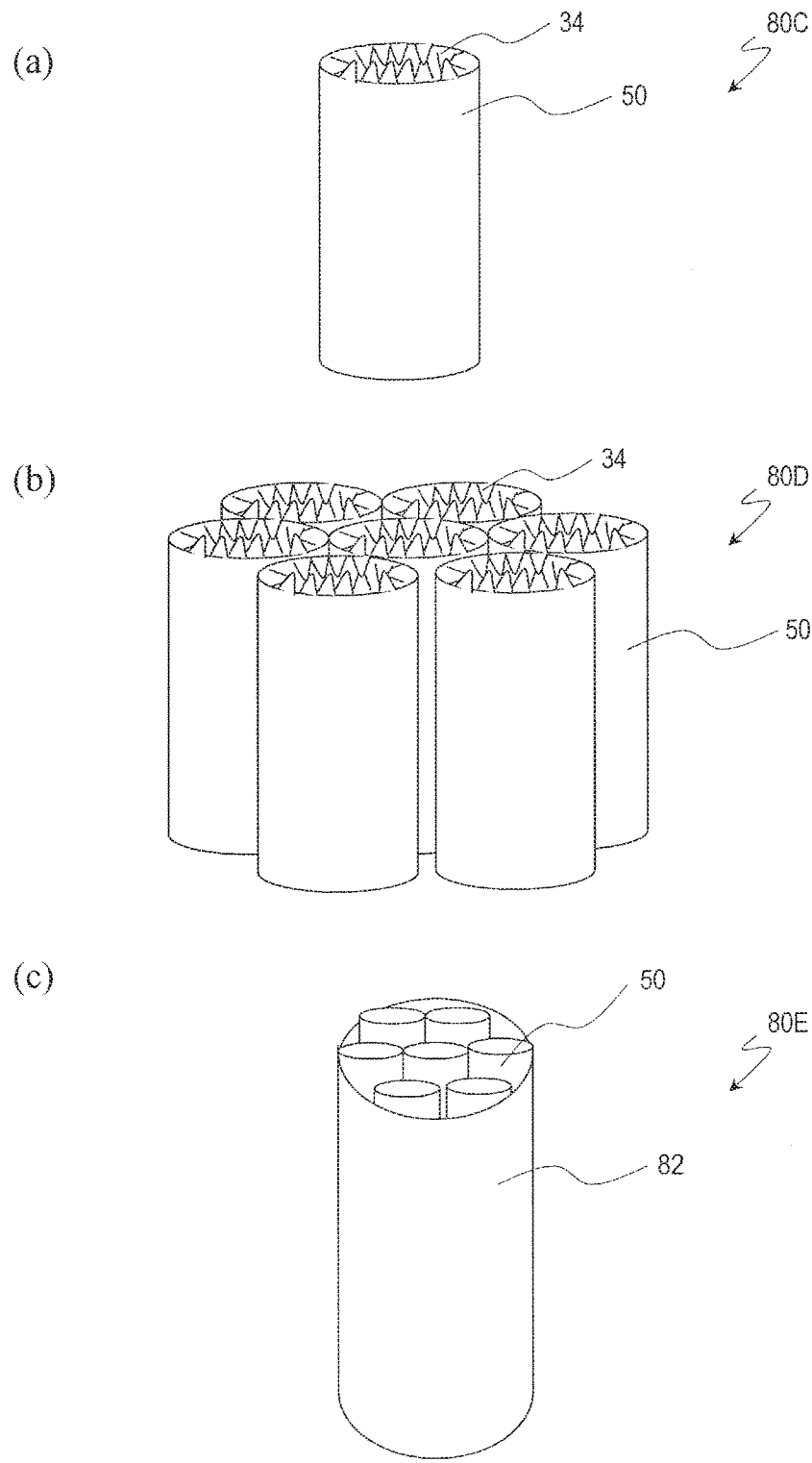
FIG. 13 (a) to (c) are schematic diagrams showing still other sterilization filters according to an embodiment of the present invention.

The sterilization filter which utilizes electrophoresis is not limited to the above-described examples but can be variously modified by utilizing, for example, the sterilization filters which have been described with reference to FIG. 12 to FIG. 13. For example, a film which has a synthetic polymer film may be rolled in many layers or may be folded or stacked. In such a case, it is preferred to form spacer portions or separately provide spacers in order to secure a sufficient space above the moth-eye structure.

A container which has a microbicidal activity can be manufactured by utilizing electrophoresis as is the sterilization filter 90A shown in FIG. 14(a).

A container 90B shown in FIG. 14(b) has a synthetic polymer film 34 on at least part of the inner walls of the main body. It has a tubular member 92 placed at the center of the main body of the container. Here, the rectangular main body of the container and the hollow cylindrical member 92 are illustrated, although these components are not limited to particular shapes. The moth-eye structure surface of the synthetic polymer film 34 provided on the inner wall of the main body of the container is supplied with a positive voltage, while the outer perimeter surface of the hollow cylindrical member 92 is supplied with a negative voltage. Accordingly, negatively-charged microorganisms m are attracted to the surface of the synthetic polymer film 34 by electrophoresis and more efficiently undergo the microbicidal activity. On the other hand, positively-charged proteins p and sodium ions are attracted to the outer perimeter surface of the hollow cylindrical member 92 in the opposite direction to the microorganisms m, so that the microorganisms m are moved away from nutrients, and the advantage of suppressing growth of the microorganisms m is obtained.

Note that the container 90B may be configured such that, contrary to the examples illustrated in FIGS. 14(a) and 14(b), the inner perimeter surface of the film 70 or the inner perimeter surface of the main body of the container is supplied with a negative voltage while the outer perimeter surface of the hollow cylindrical member 92 is supplied with a positive voltage. In this case, the surface of the synthetic polymer film 34 which has the moth-eye structure is provided at least on the outer perimeter surface of the hollow cylindrical member 92.

Hereinafter, it is explained with experimental examples that a sterilization filter according to an embodiment of the present invention has a microbicidal ability for a gas.

A sterilization filter 81 of example 1 is described with reference to FIGS. 15(a) to 15(e). FIGS. 15(a) to 15(e) are schematic diagrams for illustrating the configuration of the sterilization filter 81.

The sterilization filter 81 shown in FIG. 15(a) was manufactured as described below.

Firstly, as shown in FIG. 15(b), a transparent tube 85 which had an inside diameter of 5.5 cm and a length of 23 cm was provided.

Then, a film 71 was provided over the entire inner surface of the tube 85. That is, in the sterilization filter 81, the film 71 was arranged in the shape of a hollow cylinder with a diameter of 5.5 cm and a length of 23 cm as shown in FIG. 15(c). The film 71 had a synthetic polymer film 34 on the inner surface of the hollow cylinder. The synthetic polymer film 34 was, for example, formed on a base film (not shown).

Then, films 72 and films 73 shown in FIG. 15(d) were provided inside the tube 85 and the film 71. The films 72 and the films 73 had synthetic polymer films 34 on both sides of the base film (not shown). The films 72 were realized by transforming a film of 4 cm×15 cm or 5 cm×15 cm into a hollow cylinder. The films 72 were arranged in a direction perpendicular to the base of the hollow cylinder as shown in FIG. 15(d). Between adjoining films 72, a circular film 73 with a diameter of 5.2 cm was provided generally parallel to the base of the hollow cylinder. As shown in FIG. 15(e), through holes were formed by a needle in the film 73. The synthetic polymer films 34 of the film 71, the films 72 and the films 73 were made of the same resin material as that of the above-described sample film No. 3.

In the sterilization filter 81, the inner volume of the hollow cylinder demarcated by the synthetic polymer film 34 of the film 71 (i.e., the inner volume of the tube 85) was $(5.5/2)\times(5.5/2)\times\pi\times23$ (cm$^3$). The areas of the moth-eye structure surfaces of the film 71, the films 72 and the films 73 in the hollow cylinder were as follows: the film 71 had $5.5\times\pi\times23$ (cm$^2$), the films 72 had $15\times23\times2$ (cm$^2$), and the films 73 had $(5.2/2)\times(5.2/2)\times\pi\times4\times2$ (cm$^2$). Here, the films 72 and the films 73 had the moth-eye structure on both surfaces as previously described. The area of the moth-eye structure surface per 1 cm$^3$ of the inner volume of the sterilization filter 81 was 2.3 cm$^2$.

Figure 16:
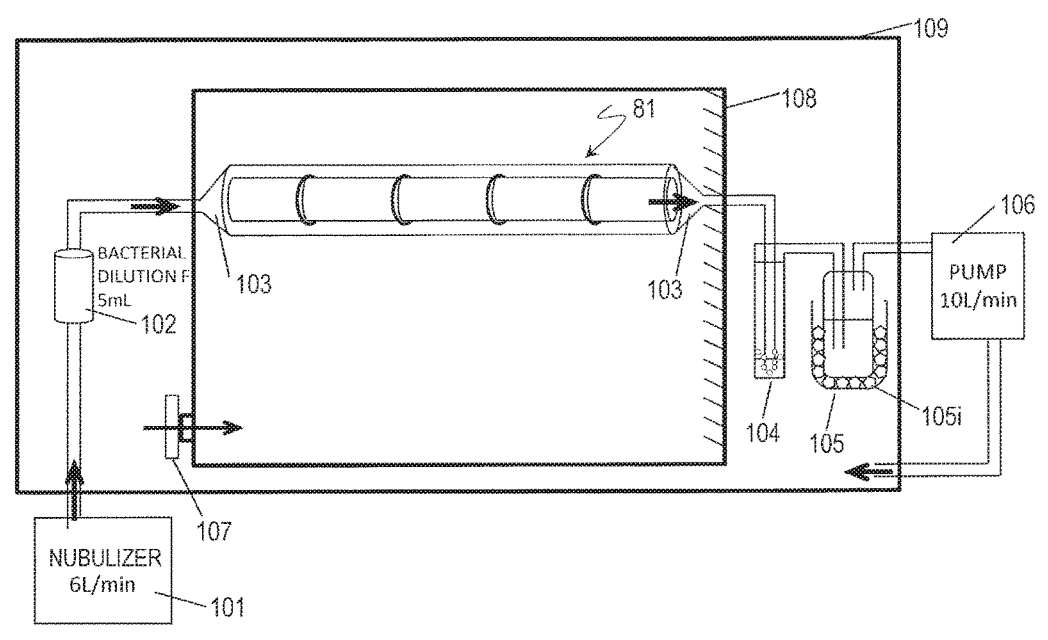

The sterilization filter 81 was placed in an experimental system shown in FIG. 16 for assessing the microbicidal ability as described below. FIG. 16 is a diagram schematically showing the experimental system. In FIG. 16, arrows represent flows of a gas.

Bacterial dilution F was prepared. 1.5E+05 CFU/mL *Bacillus subtilis* (genus: *bacillus*) bacteria were contained in Bacterial dilution F. No nutrient source was added to bacterial dilution F. *Bacillus subtilis* is a Gram-positive rod-shaped bacterium, which has spores, and is therefore resistant to drying and heat. To reduce the probability of death of bacteria due to drying, *Bacillus subtilis*, which is resistant to drying, was used.

5 mL bacterial dilution F was put in a container 102 which was provided between a nubulizer 101 and the sterilization filter 81. Bacterial dilution F was sprayed by the nubulizer 101 into the sterilization filter 81 via a funnel 103. A gas which had passed through the sterilization filter 81 was brought into 50 mL sterilized water (phosphate buffer saline (PBS)) in an impinger 104 so as to produce bubbles, whereby bacteria in the gas were collected. The spraying and collection were carried out for 15 minutes at a gas flow rate of 10 L/min. The spraying and collection were carried out at 20° C. with a humidity of 42%. The bacterium collection rate by the impinger 104 was about 20%.

The impinger 104 was coupled to a moisture absorption tank 105. The moisture absorption tank 105 was configured to absorb moisture from the gas. The moisture absorption tank 105 had an ice bath 105i in order to keep the temperature inside the moisture absorption tank 105 at 10° C. or lower. The moisture absorption tank 105 was coupled to a suction pump 106.

The sterilization filter 81 was placed in a container 108, and flowing in and out of the air was realized via a membrane filter 107. The experimental system, exclusive of the nubulizer 101 and the suction pump 106, was placed in a container 109. To prevent bacteria in the gas from being expelled out of the container 109, the container 109 had a HEPA filter (not shown).

150 μL sterilized water in the impinger 104, containing collected bacteria, was diluted 10-fold with sterilized water, whereby bacterial dilution G was prepared. 150 μL bacterial dilution G was diluted 10-fold with sterilized water, whereby bacterial dilution H was prepared. 1 mL bacterial dilution G and 1 mL bacterial dilution H were respectively spread over Petrifilm™ media (product name: Aerobic Count Plate (AC), manufactured by 3M). The bacteria were cultured in an incubator at 37° C. After 17 hours, the number of bacteria was counted. Sampling was carried out twice for each dilution. The number of bacteria was the average for the two samplings.

After the above-described spraying and collection, bacteria remaining in the sterilization filter 81 were also collected by washing the filter with 200 mL PBS. A 1 mL portion of the PBS was spread over a Petrifilm™ medium which was the same as that described above. The bacteria were cultured and counted under the same conditions as those described above.

The same experiment was performed using a sterilization filter 181 of comparative example 1 instead of the sterilization filter 81. The sterilization filter 181 of comparative example 1 was the same as the sterilization filter 81 except that the film 71, the films 72 and the films were replaced by PET films of the same shapes. The obtained results are juxtaposed in Table 3 below.

TABLE 3

| NUMBER OF VIABLE BACTERIA (CFU) | EXAMPLE 1 | COMPARATIVE EXAMPLE 1 |
|---|---|---|
| NUMBER OF VIABLE BACTERIA BEFORE SPRAYING | 490500 | 490500 |
| AFTER SPRAYING AND COLLECTION (COLLECTED BY IMPINGER) | 125000 | 177500 |
| AFTER SPRAYING AND COLLECTION (ADHERING TO STERILIZATION FILTER) | 102000 | 40000 |
| TOTAL NUMBER OF VIABLE BACTERIA AFTER SPRAYING AND COLLECTION | 227000 | 217500 |

After the spraying and collection, 1.73 mL bacterial dilution F was remaining in the container 102, and therefore, the number of viable bacteria before the spraying was considered as the number of viable bacteria in 3.27 mL bacterial dilution F. The number of viable bacteria after the spraying and collection in example 1 was 104.4% of the number of viable bacteria after the spraying and collection in comparative example 1.

Next, the same experiment as that of example 1 was performed using a sterilization filter 82 of example 2 shown in FIG. 17(a). In the sterilization filter 82 of example 2, the total area per unit volume of the surface that had the microbicidal activity was larger than in the sterilization filter 81 of example 1.

The sterilization filter 82 of example 2 is described with reference to FIGS. 17(a) to 17(c). FIGS. 17(a) to 17(c) are schematic diagrams for illustrating the configuration of the sterilization filter 82.

The sterilization filter 82 shown in FIG. 17(a) was manufactured as describe below.

Firstly, in the same way as for the sterilization filter 81 of example 1, a transparent tube 85 with an inside diameter of 5.5 cm and a length of 23 cm such as shown in FIG. 17(b) was provided, and a film 71 was provided over the entire inner surface of the tube 85. That is, as shown in FIG. 17(c), in the sterilization filter 82, the film 71 was arranged in the shape of a hollow cylinder with a diameter of 5.5 cm and a length of 23 cm. The film 71 had a synthetic polymer film 34 on the inner surface of the hollow cylinder. The synthetic polymer film 34 was provided on, for example, a base film (not shown).

Then, 40 film pieces 74 were provided inside the tube 85 and the film 71 as shown in FIG. 17(c). Each of the film pieces 74 was in the form of a strip of 1 cm×25 cm and was configured to have synthetic polymer films 34 on both sides of a base film (not shown). The synthetic polymer films 34 of the film 71 and the film pieces 74 were made of the same resin material as that of the above-described sample film No. 3.

In the sterilization filter 82, the areas of the moth-eye structure surfaces of the film 71 and the film pieces 74 in the hollow cylinder demarcated by the synthetic polymer film 34 of the film 71 were as follows: the film 71 had 5.5×π×23 (cm²), and the film pieces 74 had 1×25×40×2 (cm²). Here, the film pieces 74 had the moth-eye structure on both surfaces as previously described. The area of the moth-eye structure surface per 1 cm³ of the inner volume of the sterilization filter 82 was 4.4 cm².

An experiment was performed using the sterilization filter 82 of example 2 and a sterilization filter 182 of comparative example 2 under the same conditions as those of the above-described example 1, except for the following differences from example 1. The number of bacteria in bacterial dilution F contained in the container 102 was 3.0E+06 CFU/mL. 100 μL sterilized water in the impinger 104, containing collected bacteria, was diluted 10-fold with sterilized water, whereby bacterial dilution G was prepared. 100 μL bacterial dilution G was diluted 10-fold with sterilized water, whereby bacterial dilution H was prepared. 100 μL bacterial dilution G and 100 μL bacterial dilution H were respectively spread over agar plate media. The bacteria were cultured in an incubator at 37° C. After 17 hours, the number of bacteria was counted. In counting the number of bacteria, sampling was carried out three times for each dilution. The number of bacteria was the average for the three samplings. The sterilization filter 82 was not washed for collecting remaining bacteria therefrom. The sterilization filter 182 of comparative example 2 was the same as the sterilization filter 82 except that the film 71 was replaced by a PET film of the same shape and that the film pieces 74 were replaced by 80 PET film pieces in the form of a strip of 1 cm×12.5 cm.

The obtained results are shown in Table 4.

TABLE 4

| NUMBER OF VIABLE BACTERIA (CFU/mL) | EXAMPLE 2 | COMPARATIVE EXAMPLE 2 |
|---|---|---|
| AFTER SPRAYING AND COLLECTION | 2.5E+04 | 3.9E+04 |

The number of viable bacteria after the spraying and collection in example 2 was 64% of the number of viable bacteria after the spraying and collection in comparative example 2. It was thus proved that the sterilization filter of example 2 has a microbicidal ability against *Bacillus subtilis* bacteria contained in a gas.

The difference between example 1 and example 2 lies in the area per unit volume of the surface that has the microbicidal activity. The results of comparison between example 1 and example 2 are shown in Table 5.

TABLE 5

| | SURFACE AREA ($cm^2$) PER VOLUME 1 $cm^3$ | NUMBER OF VIABLE BACTERIA RELATIVE TO COMPARATIVE EXAMPLE (%) |
|---|---|---|
| EXAMPLE 1 | 2.3 | 104.4 |
| EXAMPLE 2 | 4.4 | 64 |

It can be seen from Table 5 that, when a sterilization filter according to an embodiment of the present invention is used for a gas, it is preferred that the area per unit volume 1 $cm^3$ of the surface that has the microbicidal activity is, for example, not less than 4.4 $cm^2$.

INDUSTRIAL APPLICABILITY

A synthetic polymer film which has a bactericidal surface and a filter or container in which such a synthetic polymer film is used according to an embodiment of the present invention are applicable to various uses including, for example, uses for sterilization of surfaces of kitchen and bathroom facilities. The synthetic polymer film which has a bactericidal surface, the filter, and the container according to an embodiment of the present invention can be produced at low cost.

REFERENCE SIGNS LIST

34A, 34B synthetic polymer film
34Ap, 34Bp raised portions
42A, 42B base film
50A, 50B, 70, 70A-70G, 72A, 72B film
60A-60D, 90B container
80A-80E, 90A sterilization filter

The invention claimed is:

1. A sterilization filter comprising a synthetic polymer film, the synthetic polymer film having a first surface which has a plurality of first raised portions and a second surface opposite to the first surface, a two-dimensional size of the plurality of first raised portions being more than 20 nm and less than 500 nm when viewed in a normal direction of the first surface, wherein the synthetic polymer film is arranged in a predetermined shape, in the arrangement of the predetermined shape, a direction normal to the second surface varies depending on a position on the second surface, and at least part of the first surface is capable of coming into contact with a gas or liquid, and wherein the synthetic polymer film further has a plurality of second raised portions superimposedly formed over the plurality of first raised portions, and a two-dimensional size of the plurality of second raised portions is smaller than the two-dimensional size of the plurality of first raised portions and does not exceed 100 nm.

2. The sterilization filter of claim 1 wherein, in the arrangement of the predetermined shape, a cross section of the synthetic polymer film forms at least one ring.

3. The sterilization filter of claim 1 wherein, in the arrangement of the predetermined shape, a cross section of the synthetic polymer film forms a spiral.

4. The sterilization filter of claim 1, wherein the predetermined shape is a bellows-like shape.

5. The sterilization filter of claim 1, wherein the first surface further has a plurality of spacer portions.

6. The sterilization filter of claim 5, wherein a height of the plurality of spacer portions is not less than 1 μm.

7. The sterilization filter of claim 5, wherein the plurality of spacer portions have a pillar-like shape.

8. The sterilization filter of claim 1, further comprising a spacer, wherein the spacer is arranged so as to form a space above the first surface of the synthetic polymer film.

9. The sterilization filter of claim 8, wherein the spacer is in the form of a thread.

10. The sterilization filter of claim 1, further comprising at least one electrode which is in contact with the synthetic polymer film.

11. The sterilization filter of claim 1, wherein at least part of the first surface of the synthetic polymer film is positively charged.

12. The sterilization filter of claim 1, wherein at least part of the second surface of the synthetic polymer film is negatively charged.

13. The sterilization filter of claim 1, wherein
the predetermined shape is a cylindrical shape,
the synthetic polymer film demarcates a cylinder, and
a plurality of synthetic polymer film pieces are provided in the cylinder, each of the plurality of synthetic polymer film pieces having a surface which has a plurality of third raised portions, a two-dimensional size of the plurality of third raised portions being more than 20 nm and less than 500 nm when viewed in a normal direction of the surface of the synthetic polymer film piece.

14. The sterilization filter of claim 13, wherein a sum of an area per 1 cm$^3$ of an inner volume of the cylinder of the first surface of the synthetic polymer film and an area per 1 cm$^3$ of an inner volume of the cylinder of the surfaces of the plurality of synthetic polymer film pieces is not less than 4.4 cm$^2$.

15. The sterilization filter of claim 13, wherein a static contact angle of the surfaces of the plurality of synthetic polymer film pieces with respect to hexadecane is not more than 51°.

16. The sterilization filter of claim 13, wherein a static contact angle of the surfaces of the plurality of synthetic polymer film pieces with respect to hexadecane is not more than 31°.

17. The sterilization filter of claim 13, wherein a static contact angle of the surfaces of the plurality of synthetic polymer film pieces with respect to water is not more than 131°.

18. The sterilization filter of claim 1, wherein a static contact angle of the first surface of the synthetic polymer film with respect to hexadecane is not more than 51°.

19. The sterilization filter of claim 1, wherein a static contact angle of the first surface of the synthetic polymer film with respect to hexadecane is not more than 31°.

20. The sterilization filter of claim 1, wherein a static contact angle of the first surface of the synthetic polymer film with respect to water is not more than 131°.

21. The sterilization filter of claim 1, wherein the synthetic polymer film has a through hole.

22. The sterilization filter of claim 1, wherein the plurality of first raised portions include a generally conical portion.

* * * * *